(12) United States Patent
Batarilo et al.

(10) Patent No.: US 12,383,668 B2
(45) Date of Patent: Aug. 12, 2025

(54) MULTI-FLUID DELIVERY SYSTEM

(71) Applicant: ACIST MEDICAL SYSTEMS INC., Eden Prairie, MN (US)

(72) Inventors: Zvonimir Batarilo, Lausanne (CH); Dieter Heidmann, Geretsried (DE); Jan Sievertsen, Munich (DE)

(73) Assignee: ACIST MEDICAL SYSTEMS INC., Eden Prairie, MN (US)

( * ) Notice: Subject to any disclaimer, the term of this patent is extended or adjusted under 35 U.S.C. 154(b) by 683 days.

(21) Appl. No.: 17/787,683

(22) PCT Filed: Sep. 10, 2020

(86) PCT No.: PCT/EP2020/075284
§ 371 (c)(1),
(2) Date: Jun. 21, 2022

(87) PCT Pub. No.: WO2021/129959
PCT Pub. Date: Jul. 1, 2021

(65) Prior Publication Data
US 2023/0011814 A1 Jan. 12, 2023

(30) Foreign Application Priority Data
Dec. 23, 2019 (EP) ..................................... 19219196

(51) Int. Cl.
*A61M 5/14* (2006.01)
*A61M 5/00* (2006.01)
*A61M 5/142* (2006.01)

(52) U.S. Cl.
CPC .......... *A61M 5/1408* (2013.01); *A61M 5/007* (2013.01); *A61M 5/1422* (2013.01)

(58) Field of Classification Search
CPC .. A61M 5/1408; A61M 5/007; A61M 5/1422; A61M 2005/3123;
(Continued)

(56) References Cited

U.S. PATENT DOCUMENTS 4,065,230 A * 12/1977 Gezari ................ A61M 5/1422
604/152
4,750,869 A * 6/1988 Shipman, III ............ F17C 5/06
417/345
(Continued)

FOREIGN PATENT DOCUMENTS

DE  102011120105 A1  6/2013
EP       1035882 B1  6/2004
(Continued)

OTHER PUBLICATIONS

International Search Report and Written Opinion for PCT/EP2020/075284, mailed Jan. 28, 2021.

*Primary Examiner* — Cris L. Rodriguez
(74) *Attorney, Agent, or Firm* — VIVICAR Law, PLLC

(57) ABSTRACT

A fluid delivery system is disclosed which comprises at least one first supply station for supplying a first fluid and at least one second supply station for supplying a second fluid different from the first fluid. The fluid delivery system further comprises a pressurizing unit for pressurizing the first and second fluids, said pressurizing unit comprising first and second pump modules, and each pump module comprising a chamber and a piston provided with a plunger to define first and second variable-volume sub-chambers. The fluid delivery system further comprises first and second inlet fluid circuits, first and second outlet fluid circuits, and a first recirculation fluid pathway fluidically connecting the first and second variable-volume sub-chambers of a pump module. Moreover, a first actuator is associated to said first recirculation fluid pathway for managing the fluid passage in both directions between said first and second variable-volume sub-chambers of said pump module. Methods of operating the fluid delivery system are disclosed too.

11 Claims, 14 Drawing Sheets

(58) Field of Classification Search
CPC .. A61M 2005/1402; A61M 2005/1403; A61M 2205/7536
See application file for complete search history.

(56) References Cited

U.S. PATENT DOCUMENTS

| | | | |
|---|---|---|---|
| 5,411,374 A | | 5/1995 | Gram |
| 5,551,488 A | | 9/1996 | Gram |
| 5,616,005 A | * | 4/1997 | Whitehead ................ F04F 1/10 |
| | | | 417/393 |
| 6,135,719 A | | 10/2000 | Yoder et al. |
| 2007/0196219 A1 | * | 8/2007 | Hofling ................ F04B 15/023 |
| | | | 417/347 |
| 2011/0123363 A1 | * | 5/2011 | Marica .................... F04B 9/105 |
| | | | 417/279 |
| 2012/0053557 A1 | | 3/2012 | Abal |
| 2014/0224829 A1 | * | 8/2014 | Capone ............... B05B 11/1015 |
| | | | 222/23 |
| 2014/0257097 A1 | * | 9/2014 | Bonnette ............... F04B 9/1095 |
| | | | 600/432 |
| 2022/0409808 A1 | | 12/2022 | Batarilo et al. |
| 2023/0084243 A1 | | 3/2023 | Batarilo et al. |

FOREIGN PATENT DOCUMENTS

| | | | |
|---|---|---|---|
| WO | 9015632 A1 | 12/1990 | |
| WO | 2008126035 A1 | 10/2008 | |
| WO | 2015084302 A1 | 6/2015 | |
| WO | 2016033351 A2 | 3/2016 | |
| WO | 2017114706 A1 | 7/2017 | |
| WO | WO-2021150340 A1 * | 7/2021 | .......... A61M 5/1408 |

* cited by examiner

MULTI-FLUID DELIVERY SYSTEM

CROSS-REFERENCE TO RELATED APPLICATIONS

This application is the national stage application of corresponding international application number PCT/EP2020/075284, filed Sep. 10, 2020, which claims priority to and the benefit of European application no. 19219196.3, filed Dec. 23, 2019, which is hereby incorporated by reference in its entirety.

TECHNICAL FIELD

The present disclosure relates to the field of fluid delivery. More specifically, the present disclosure relates to a fluid delivery system which allows delivery of two or more fluids under predetermined and desired operating conditions. Even more specifically, the present disclosure relates to an injection system and methods for injecting at least two different medical fluids.

BACKGROUND ART

The background of the present disclosure is hereinafter introduced with the discussion of techniques relating to its context. However, even when this discussion refers to documents, acts, artifacts and the like, it does not suggest or represent that the discussed techniques are part of the prior art or are common general knowledge in the field relevant to the present disclosure.

Delivery systems for administering a liquid composition by injection or by infusion are known in the art.

For instance, the injection of fluids into patients is commonplace in several medical procedures. For example, a contrast agent (or contrast medium) may be injected, possibly along with a saline solution, to enhance contrast of target (body) features (for example, human body's structures or organs) within a patient during scan examinations thereof. Particularly, in imaging applications (wherein a visual representation of the interior of the patient is created in a non-invasive way without turning to surgery techniques) the use of a contrast agent makes the target features more conspicuous. As a result, target features that would otherwise be less distinguishable from other nearby features (for example, surrounding tissues) are advantageously highlighted. This significantly facilitates the task of clinicians in diagnostic applications, and particularly in the identification and/or characterization of lesions, the monitoring of their evolution or the response to medical treatments. For example, an iodine-based contrast agent (such as comprising iopamidol) is commonly used in Computed Tomography (CT) applications (such as angiography investigations).

The contrast agent is usually injected into a blood vessel of a patient preferably by an automated injection system. The injection system pressurizes the contrast agent and injects it into the patient's vasculature or organ under predetermined injection conditions, for example at a predetermined flow rate, a predetermined volume and a predetermined pressure. In this way, the contrast agent may be injected in a controlled, safe and efficient manner.

Therefore, an injection system is typically provided with one or more supply stations for supplying the contrast agent and/or the saline solution from a corresponding container (e.g. a bottle, a bag or a pouch). The injection system is further provided with a delivery arrangement (i.e. a combination of tubing lines) that is in fluid communication with the at least one supply station and a pressurizing unit. Since the delivery arrangement is positioned upstream of the pressurizing unit and, therefore, it is not in direct connection with a patient, with substantially no risk or a very low risk of cross-contamination, generally the delivery arrangement is a disposable element that is discarded periodically (for example, every 10 or 12 hours). This means that the delivery arrangement is not changed when a new patient undergoes an examination and it is typically kept in place for multiple successive injections (and thus multiple successive patients), till the predetermined period of time designed for that delivery arrangement is fully elapsed.

The powered injection systems known in the art and presently available on the market are categorized into two major groups: syringe injectors (like Empower CTA® or Empower CTA®+ manufactured by Bracco Injeneering SA) and syringe-less injectors (like CT Exprès® manufactured by Bracco Injeneering SA).

Syringe injectors can benefit from the syringe/piston technology which guarantees remarkably high-pressure fluid injection as well as fluid delivery accuracy and precision. Nevertheless, syringe injectors have some drawbacks which are mainly related to a cumbersome syringe workflow (in terms of loading and unloading of the syringes at the injector head, filling of the syringes with the fluid to be injected, priming and purging the syringes), to syringes (i.e. disposables) cost which is far from being negligible, and to troublesome waste management (i.e. inevitably discarding the expensive contrast agent that has not been injected to the patient and that has remained in the non-reusable syringes).

On the contrary, syringe-less injectors can benefit from a more efficient and lean workflow since the use of bottles/bags (in place of syringes) provides for higher quantities of contrast agent which is rendered available for serving multiple patients, thereby making waste management easier because only a disposable patient line is discarded every new incoming patient and contrast agent waste is remarkably reduced. Nevertheless, since the main technology used in the syringe-less injectors is a peristaltic pump—either as a disposable peristaltic pump or as a reusable peristaltic pump—due to its intrinsic nature, this technology does not allow to achieve significantly high pressures and flow rates (especially in the peristaltic pump disposable version) in comparison with the syringe injectors, and in operation it may also generate some disadvantageous fluctuations of the flow rate and/or of the pressure which, at some extent, may contribute in decreasing the delivery accuracy of the fluid delivery system.

Recently, some specific medical procedures have also required that the powered injectors can provide for high demanding hydraulic performances, in particular in terms of pressure and flow rate of the fluid to be injected into a patient.

For example, it has become more and more frequent that a powered injector is requested to be connected to implantable devices (e.g. PICC & PORT) which are already implanted in a patient's vasculature and which are used for establishing an intravascular access to a patient.

PICC is a Peripherally Inserted Central Catheter that is typically placed in a patient's arm to allow for a prolonged intravenous access, such as for extended antibiotic treatment or chemotherapy. A PICC is inserted in a peripheral vein (e.g. the cephalic vein, the basilic vein or the brachial vein) and then advanced through increasingly larger veins towards the heart, until the catheter tip rests in the distal superior vena cava or cave-atrial junction while the proximal end of the PICC remains outside of the body. A PICC is typically left in place in the patient's arm for periods ranging from six weeks to one year.

A PORT usually comprises a reservoir (the portal)—that is provided with a septum for needle insertion—and a catheter that goes from the reservoir into a patient's vein. The reservoir is surgically inserted under the skin in the upper chest or in the arm, and the catheter is fully inserted into the vein, i.e. there's no catheter tail outside of the patient's body.

Therefore, some patients that need to undergo an imaging examination (e.g. a computed tomography—CT) may already have a PICC & PORT in place for other purposes. Thus, already in place multi-lumen PICCs may be advantageously used by the healthcare personnel for power injection of diagnostic and/or therapeutic agents. However, the presence of said implanted devices inevitably represents a technical constraint for a powered injector (especially for a powered syringe-less injector) that is requested to generate pressure and flow rate values sufficiently high for still ensuring the desired and predetermined injection performances, even when said implanted devices are interposed between the injection system and the patient.

WO 2016/033351 discloses an infusion system which comprises a double action infusion pump. The pump includes a cylinder and a reciprocating piston received within the cylinder, the reciprocating piston separating a first pump chamber from a second pump chamber of the cylinder. A reciprocating motor is coupled with the reciprocating piston, and the first and second pump chambers alternate between filling and evacuating conditions with reciprocation of the reciprocating piston through operation of the reciprocating motor, and the speed of reciprocation is varied to provide a continuous output of fluid between the first and second pump chambers. A fluid source and a catheter are optionally coupled with the double action infusion pump. The catheter includes one or more infusion ports near a catheter distal portion, and the one or more infusion ports receive and expel the continuous output of fluid from the double action infusion pump.

DE 10 2011 120 105 discloses a device having a container with an opening, in which a movable piston is arranged. A piston rod is provided to displace the piston in the container. The container is divided into chambers. A flexible sealing element is provided to close the opening of the container. Two inlet ducts are communicated with a media feed line and the chambers respectively. Two outlet ducts are communicated with the media feed line and the chambers respectively.

Technical fields different from medical applications may as well require delivery of compositions under specific and predetermined conditions.

For instance, a glue formulation may require to be delivered only when suitable operating conditions are guaranteed, e.g. when a given homogeneity of the glue formulation components is achieved. Therefore, a dedicated delivery system for applying the glue formulation in a given environment should ensure that the glue formulation is actually delivered only when said desired homogeneity is obtained, so that efficient and correct functioning of the glue can be obtained.

Ensuring a desired homogeneity is required, for instance, also in the processes for the preparation of a painting composition or of a coating composition that are carried out immediately before application thereof, particularly in the automotive, aerospace, housing fixtures industries.

According to further possible applications, a delivery system may be required to start delivering a given composition only when a specific property threshold thereof is achieved, for instance when a predetermined temperature value has been reached. Therefore, the delivery system should ensure that said temperature value is effectively obtained and, moreover, that a proper (typically slow) heat distribution has occurred within said composition.

The aspects mentioned above are applicable not only to traditional industries (like pharma, chemical, automotive, aerospace industries) where a mixing or shaking step is requested to be performed before a final delivery/application step is executed. Indeed, also cellular/biological applications may require that predetermined conditions are maintained or achieved before moving to a successive step. For instance, many experiments involving cells cultures make use of bovine serum which is typically required to be regularly mixed by careful swirling before use in order to keep its native structural state.

The Applicant has thus perceived the need of improving the hydraulic performance of a fluid delivery system which ensures that two or more different (i.e. distinct) fluids can be delivered at a sufficiently high pressure (if required) and at a sufficiently high flow rate (if required), meanwhile guaranteeing high accuracy and high precision during delivery thereof.

With specific reference to the medical field, and more particularly with reference to the injection or infusion into a patient's body (generally into a patient's blood vessel that reaches a body portion or a patient's body organ to be treated and/or analyzed, e.g. through scan examinations like X-ray, CT, MRI or ultrasound exams) of liquid medicaments or of diagnostically active contrast agents, the Applicant has perceived the need of improving the hydraulic performance of a powered injector (mainly in terms of maximum pressure and maximum flow rate of the injected fluid) so that a predetermined injection procedure is not affected by any possible additional medical device (e.g. PICC & PORT) already implanted in the patient's body and to which the powered injector is requested to be connected.

Moreover, the need of improving the hydraulic performance of a powered injector is also correlated to the fact that more and more viscous contrast agents are made available on the market, such increased viscosity generally decreasing the injector delivery performance in terms of maximum pressure and maximum flow rate of the injected fluid. Even worst, sometimes said delivery performance is adversely affected also by the habit in some specific countries of injecting the fluid at room temperature, i.e. without pre-warming it at about body temperature before injection, said pre-warming indeed advantageously contributing in reducing the viscosity of said contrast agents.

The Applicant has also perceived the need of improving the capability of a fluid delivery system to deliver a fluid satisfying specific and predetermined fluid properties which are requested for a proper use of that fluid. In other words, the Applicant has perceived the need of providing a fluid delivery system which satisfies and guarantees the required delivery conditions for the specific fluid to be delivered, meanwhile ensuring that the delivery system is accurate, precise, efficient, reliable and simple as far as easiness of use and manufacturing process thereof are concerned.

The Applicant has also perceived the need of improving the delivery performance and accuracy of a fluid delivery system that is requested to sequentially and/or alternately deliver at least two different fluids having different characteristics/properties (e.g. contrast agents with different viscosities, a saline solution, a mixture thereof). In fact, delivering at least two different fluids in alternate sequence requires corresponding alternate opening/closing steps of the different fluid pathways through which said fluids are made to flow, said steps possibly causing the generation of air bubbles within said fluid pathways due to cavitation phenomena, and possibly generating also under- or overpressure events that may negatively impact the fluid flow rate, for instance in terms of the desired flow rate value to be provided by the fluid delivery system and/or in terms of ensuring regularity and continuity of the fluids flows. Moreover, the alternate opening/closing steps of the different fluid pathways require that valves or clamps are operated on the high-pressure side of the fluid flow, said aspect being very challenging and demanding for a very precise and accurate functioning of the fluid delivery system.

SUMMARY

A simplified summary of the present disclosure is herein presented to provide a basic understanding thereof; however, the sole purpose of this summary is to introduce some concepts of the disclosure in a simplified form as a prelude to its following more detailed description, and it is not to be interpreted as an identification of its key elements nor as a delineation of its scope.

In order to provide a fluid delivery system which can ensure to deliver at least two different fluids, and to accurately and precisely achieve for each fluid the desired/predetermined delivery conditions (e.g. in terms of pressure and flow rate), the Applicant has found to provide a fluid delivery system with at least two pump modules, each pump module processing at least one fluid, at least one pump module comprising a dedicated recirculation fluid circuit (sometimes also defined in the present description as recirculation fluid pathway) for recirculating at least one fluid internally to the corresponding pump module when, during operation of the fluid delivery system, said at least one fluid is requested not to be delivered outside of the fluid delivery system (i.e. not to be discharged from said pump module and thus not to be delivered by the fluid delivery system).

Therefore, an aspect of the present disclosure provides for a fluid delivery system comprising:
  at least one first supply station for supplying a first fluid and at least one second supply station for supplying a second fluid, said second fluid being different from said first fluid;
  a pressurizing unit for pressurizing the first fluid and the second fluid comprising:
    a first pump module comprising a first chamber and a first piston contained therein, said first piston having a first plunger that, in cooperation with internal walls of said first chamber, defines first and second variable-volume sub-chambers of said first chamber, and
    a second pump module comprising a second chamber and a second piston contained therein, said second piston having a second plunger that, in cooperation with internal walls of said second chamber, defines first and second variable-volume sub-chambers of said second chamber;
  a first inlet fluid circuit in fluid communication with said at least one first supply station and with said first pump module for supplying said first fluid to said first and second variable-volume sub-chambers of said first chamber;
  a second inlet fluid circuit in fluid communication with said at least one second supply station and with said second pump module for supplying said second fluid to said first and second variable-volume sub-chambers of said second chamber;
  a first recirculation fluid circuit fluidically connecting said first and second variable-volume sub-chambers of said first chamber, and
  a first actuator for managing a fluid passage in both directions between said first and second variable-volume sub-chambers of said first chamber, said first actuator being part of said first recirculation fluid circuit.

According to a further embodiment of the present disclosure, in order to provide a fluid delivery system which can ensure to deliver at least two different fluids, and to accurately and precisely achieve for each fluid the desired/predetermined delivery conditions (e.g. in terms of pressure and flow rate), the Applicant has found to provide a fluid delivery system with at least two pump modules, each pump module processing at least one fluid and each pump module comprising a dedicated recirculation fluid circuit (sometimes also defined in the present description as recirculation fluid pathway) for recirculating said at least one fluid internally to the corresponding pump module when, during operation of the fluid delivery system, said at least one fluid is requested not to be delivered outside of the fluid delivery system (i.e. not to be discharged from said pump module and finally delivered by the fluid delivery system).

Moreover, the Applicant has also found a method of operating a fluid delivery system for delivering at least a first fluid and a second fluid, said first fluid being different from said second fluid, said method comprising the step of delivering (outside of the fluid delivery system) one of the first or the second fluid while the other fluid is recirculated internally to the fluid delivery system. According to this method, the step of delivering and the step of recirculating are inverted as soon as the other fluid is requested to be delivered outside of the fluid delivery system.

Therefore, a further aspect of the present disclosure provides for a method of operating a fluid delivery system for delivering at least a first fluid and a second fluid, said first fluid being different from said second fluid, said method comprising:
  a step of delivering the second fluid outside of the fluid delivery system;
  a step of recirculating the first fluid internally to the fluid delivery system, and
  a step of delivering the first fluid outside of the fluid delivery system.

An alternative aspect of the present disclosure provides for a method of operating a fluid delivery system for delivering at least a first fluid and a second fluid, said first fluid being different from said second fluid, said method comprising:
  a step of delivering the first fluid outside of the fluid delivery system;
  a step of recirculating the second fluid internally to the fluid delivery system;
  a step of delivering the second fluid outside of the fluid delivery system, and
  a step of recirculating the first fluid internally to the fluid delivery system.

An alternative aspect of the present disclosure provides for a method of operating a fluid delivery system comprising at least one first supply station for supplying a first fluid and at least one second supply station for supplying a second fluid, said second fluid being different from said first fluid, said fluid delivery system further comprising a pressurizing unit provided with a first pump module and a second pump module, each first and second pump module respectively comprising a chamber and a piston reciprocating therein, said piston having a plunger which, in cooperation with inner walls of said chamber, defines first and second variable-volume sub-chambers, the fluid delivery system further comprising a first (60; 260) recirculation fluid pathway and a first actuator associated thereto for fluidically connecting said first and second variable-volume sub-chambers of said first chamber, said method comprising the steps of:

supplying the first fluid from the first supply station to said first and second variable-volume sub-chambers of said first chamber;

supplying the second fluid from the second supply station to said first and second variable-volume sub-chambers of said second chamber;

axially translating the respective pistons within said first and second chambers, and operating the first actuator for recirculating the first fluid within the first chamber.

According to a further embodiment, the Applicant has also found a method of operating a fluid delivery system for delivering a first fluid and a mixture of said first fluid with a second fluid, said first fluid being different from said second fluid, said method comprising: a) a step of delivering (outside of the fluid delivery system) said first fluid; b) a step of recirculating internally to the fluid delivery system said first fluid and said second fluid for obtaining a mixture thereof, said step of recirculating said first fluid and said second fluid being preferably performed substantially simultaneously to the step of delivering the first fluid; c) a step of delivering said mixture outside of the fluid delivery system, and d) a step of recirculating internally to the fluid delivery system said first fluid, said step of recirculating the first fluid being preferably performed substantially simultaneously to said step of delivering said mixture.

According to an alternative embodiment, the Applicant has also found a method of operating a fluid delivery system for delivering a first fluid and a mixture of said first fluid with a second fluid, said first fluid being different from said second fluid, said method comprising: a) a step of delivering (outside of the fluid delivery system) said first fluid; b) a step of recirculating internally to the fluid delivery system said first fluid and said second fluid for obtaining a mixture thereof, said step of recirculating being preferably performed substantially simultaneously to the step of delivering the first fluid, and c) a step of delivering said mixture outside of the fluid delivery system.

More specifically, one or more aspects of the present disclosure are set out in the independent claims, and advantageous features thereof are set out in the dependent claims, with the wording of all the claims that is herein incorporated verbatim by reference (with any advantageous feature provided with reference to any specific aspect that applies mutatis mutandis to every other aspect).

BRIEF DESCRIPTION OF THE DRAWINGS

The solutions of the present disclosure, as well as further features and the advantages thereof, will be best understood with reference to the following detailed description thereof, given purely by way of a non-restrictive indication, to be read in conjunction with the accompanying drawings (wherein, for the sake of simplicity, corresponding elements are denoted with equal or similar references and their explanation is not repeated, and the name of each entity is generally used to denote both its type and its attributes, such as value, content and representation). In this respect, it is expressly intended that the figures are not necessary drawn to scale (with some details that may be exaggerated and/or simplified) and that, unless otherwise indicated, they are merely used to illustrate the structures and procedures described herein conceptually. Particularly.

DETAILED DESCRIPTION

Figure 1:
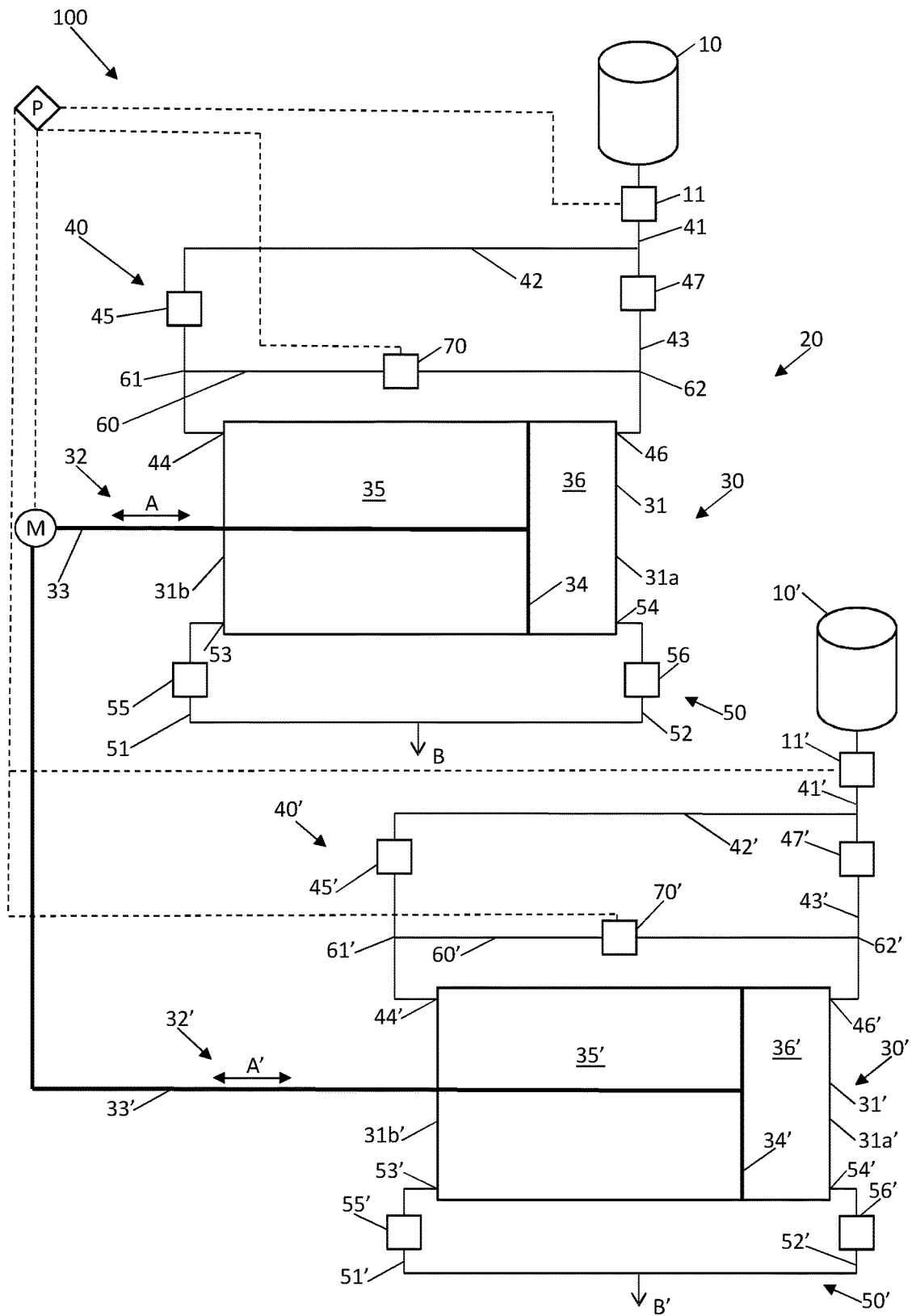
FIG. 1 shows a schematic representation of a fluid delivery system according to an embodiment of the present disclosure wherein two pump modules are arranged in parallel.

With reference to FIG. 1, a schematic representation is shown of a fluid delivery system 100 according to an embodiment of the present disclosure wherein two pump modules 30, 30' are arranged in parallel. Fluid delivery system 100 is used for delivering a first fluid contained in a first supply station 10 and a second fluid contained in a second supply station 10', wherein said first fluid and said second fluid are different from each other.

In case fluid delivery system 100 is an injection system for being used in the medical field, the first fluid contained in first supply station 10 and to be injected into a patient's vascular system can be, for instance, a contrast agent which is administered for enhancing contrast of target (body) features (for example, human body's structures or organs) within the patient during scan examinations thereof, e.g. during CT, MiII or ultrasound exams. Particularly, in imaging applications (wherein a visual representation of the interior of a patient is created in a non-invasive way without turning to surgery techniques) the use of a contrast agent makes the target features more conspicuous. As a result, target features that would otherwise be less distinguishable from other nearby features (for example, surrounding tissues) are advantageously highlighted. This significantly facilitates the task of clinicians in diagnostic applications, and particularly the identification and/or characterization of lesions, the monitoring of their evolution or response to medical treatments. For example, in CT applications the contrast agent may be an iodine-based contrast agent comprising diatrizoate, ioxaglate, iopamidol, iohexol, ioxilan, iopromide or iodixanol. An example of a commercial contrast agent comprising iopamidol is ISOVUE®, manufactured by Bracco Diagnostics Inc.®

According to an embodiment of the present disclosure, fluid delivery system 100 is configured for delivering Ultrasound Contrast Agents (USCA) in a continuous injection/infusion mode and/or as a bolus. In particular, fluid delivery system 100 is used for delivering a liquid composition which comprises a suspension of microparticles homogeneously distributed in a liquid carrier, preferably an aqueous liquid carrier, said microparticles containing entrapped pure gases or gas mixtures including at least one physiologically acceptable halogenated gas. This halogenated gas is preferably selected among $CF_4$, $C_2F_6$, $C_3F_8$, $C_4F_8$, $C_4F_{10}$, $C_5F_{12}$, $C_6F_{14}$ or $SF_6$. The gas mixtures can also contain gases such as air, oxygen, nitrogen, helium, xenon or carbon dioxide. In several cases said microparticles (microbubbles or microballoons) contain mixtures of nitrogen or air with at least one perfluorinated gas in proportions which may vary between 1 and 99%. An example of a commercial contrast agent that is used in Contrast Enhanced Ultrasound (CEUS) applications is SonoVue® (Sulphur hexafluoride microbubbles), manufactured by Bracco Suisse®.

Still referring to the medical field, the second fluid contained in second supply station 10' and to be injected into a patient's vascular system can be, for instance, a saline solution comprising a physiological or isotonic solution (e.g. sodium chloride). Alternatively, said first fluid and/or said second fluid can be a liquid medicament or a drug.

As already mentioned above, fluid delivery system 100 of the present disclosure can be used for delivering fluids in many technological fields, not necessarily strictly correlated to the medical/diagnostic field. For instance, the first fluid and the second fluid contained, respectively, in first and second supply stations 10, 10' can be two or more components of a glue formulation, of a painting formulation, of a coating formulation, or of a substance/formulation for which a delivery property (e.g. temperature) is requested to be properly reached/controlled.

Fluid delivery system 100 comprises a pressurizing unit 20 which operates on the first fluid and the second fluid so that, alternately, they will be delivered outside of the fluid delivery system (at a predetermined pressure and flow rate, previously set up by the operator or by the fluid delivery system control unit, based on the requirements designed for the specific delivery use) and recirculated within the fluid delivery system, as it will be disclosed in detail in the following of the present description. Pressurizing unit 20 comprises first pump module 30, second pump module 30' and a driving unit M which is associated to the two pump modules for operation/actuation thereof. Each pump module 30, 30' respectively comprises a chamber 31, 31' within which a piston 32, 32' is reciprocated (i.e. moved back and forth—see double arrows A, A') by driving unit M. According to the embodiment shown in the figures, chambers 31, 31' are represented as cylindrical barrels (e.g. like a syringe barrel); however other different configurations suitable for the purpose can be envisaged as well. Each piston 32, 32' respectively comprises a piston rod 33, 33' and a plunger 34, 34', the plunger being arranged to be substantially perpendicular to the piston rod and having a radial extension which substantially corresponds to the chamber radial extension (i.e. to chamber width). Therefore, in cooperation with the internal walls of said chambers 31, 31', each plunger 34, 34' defines respective first sub-chambers 35, 35' on one side of the plunger (on the left side of the plungers in the embodiment of FIG. 1) and respective second sub-chambers 36, 36' on the opposite side of the plunger (on the right side of the plungers in the embodiment of FIG. 1). During operation of fluid delivery system 100, piston 32, 32' is moved back and forth (see double arrow A, A') and thus the overall volume of said first 35, 35' and second 36, 36' sub-chambers is continuously and alternately changing, these sub-chambers being variable-volume sub-chambers. For instance, when piston 32, 32' is moved to the right in FIG. 1, the volume of first sub-chambers 35, 35' is increased while the volume of second sub-chambers 36, 36' is decreased; on the contrary, when piston 32, 32' is moved to the left in FIG. 1, the volume of second sub-chambers 36, 36' is increased while the volume of first sub-chambers 35, 35' is decreased. According to the embodiment shown in FIG. 1, plunger 34, 34' is provided at an axial end of piston rod 33, 33' (i.e. at the axial end opposite to the axial end that is connected to driving unit M). Alternatively, plunger 34, 34' can be provided at a different position along the longitudinal extension of piston rod 33, 33' (embodiment not shown in the figures) with the proviso that base walls 31a, 31b of chamber 31 as well as base walls 31a', 31b' of chamber 31' allow a sealed axial movement of piston rod 33, 33' therethrough (i.e. through said chambers).

Fluid delivery system 100 of the present disclosure further comprises a first inlet fluid circuit 40 and a second inlet fluid circuit 40'. In detail, first inlet fluid circuit 40 is in fluid communication with first supply station 10 and with first pump module 30, and analogously second inlet fluid circuit 40' is in fluid communication with second supply station 10' and with second pump module 30'. First inlet fluid circuit 40 comprises inlet fluid pathways which supply the first fluid (contained in first supply station 10) to first variable-volume sub-chamber 35 and to second variable-volume sub-chamber 36 so that chamber 31 is filled with a suitable volume amount of the first fluid to be delivered outside fluid delivery system 100 (arrow B). Analogously, second inlet fluid circuit 40' comprises inlet fluid pathways which supply the second fluid (contained in second supply station 10') to first variable-volume sub-chamber 35' and to second variable-volume sub-chamber 36' so that chamber 31' is filled with a suitable volume amount of the second fluid to be delivered outside fluid delivery system 100 (arrow B').

In detail, first and second inlet fluid circuits 40, 40' comprise a first inlet fluid pathway 41, 41' which is in fluid communication with supply station 10, 10', said first inlet fluid pathway 41, 41' including a supply station valve 11, 11' that allows the respective fluid to be discharged from supply station 10, 10'. Supply station valve 11, 11' is an active valve that is operated by the fluid delivery system, as it will be explained in detail in the following of the present description.

Downstream from supply station valve 11, 11', first and second inlet fluid circuits 40, 40' branch into a second inlet fluid pathway 42, 42' and a third inlet fluid pathway 43, 43' which are in fluid communication with first sub-chamber 35, 35' and second sub-chamber 36, 36', respectively. First sub-chamber 35, 35' is provided with a first inlet port 44, 44' which allows second inlet fluid pathway 42, 42' to be in fluid communication with first sub-chamber 35, 35'. Analogously, second sub-chamber 36, 36' is provided with a second inlet port 46, 46' which allows third inlet fluid pathway 43, 43' to be in fluid communication with second sub-chamber 36, 36'.

Upstream from the first inlet port 44, 44', second inlet fluid pathway 42, 42' is provided with a first inlet fluid circuit valve 45, 45' which allows the respective fluid (i.e. the first fluid exiting from first supply station 10 and the second fluid exiting from second supply station 10') to flowing into first sub-chamber 35, 35' through second inlet fluid pathway 42, 42'. According to an embodiment of the present disclosure, first inlet fluid circuit valve 45, 45' is a check valve, i.e. a one-way valve which allows the fluid to flow through it in only one direction, specifically from supply station 10, 10' towards first sub-chamber 35, 35', and avoiding that the fluid flows back towards supply station 10, 10'.

Analogously, upstream from second inlet port 46, 46', third inlet fluid pathway 43, 43' is provided with a second inlet fluid circuit valve 47, 47' which allows the respective fluid (i.e. the first fluid exiting from first supply station 10 and the second fluid exiting from second supply station 10') to flow into second sub-chamber 36, 36' through third inlet fluid pathway 43, 43'. According to an embodiment of the present disclosure, second inlet fluid circuit valve 47, 47' is a check valve, i.e. a one-way valve which prevents reverse flow, thereby allowing the fluid to flow through it in only one direction, specifically from supply station 10, 10' towards second sub-chamber 36, 36', and avoiding that the fluid flows back towards supply station 10, 10'.

Preferably, first 45, 45' and second 47, 47' inlet fluid circuit valves are ball check valves wherein a ball is present inside the body valve for regulating the fluid flow.

Fluid delivery system 100 of the present disclosure further comprises a first outlet fluid circuit 50 (which is separate from first inlet fluid circuit 40) and a second outlet fluid circuit 50' (which is separate from second inlet fluid circuit 40'). In detail, first outlet fluid circuit 50 is in fluid communication with first pump module 30, and analogously second outlet fluid circuit 50' is in fluid communication with second pump module 30'. Both first and second outlet fluid circuits 50, 50' comprise a first outlet fluid pathway 51, 51' and a second outlet fluid pathway 52, 52' that allow fluid delivery system 100 to discharge the first fluid from chamber 31 (see arrow B) and the second fluid from chamber 31' (see arrow B'), respectively. In detail, first sub-chamber 35, 35' is provided with a first outlet port 53, 53' which allows first outlet fluid pathway 51, 51' to be in fluid communication with said first sub-chamber 35, 35'. Analogously, second sub-chamber 36, 36' is provided with a second outlet port 54, 54' which allows second outlet fluid pathway 52, 52' to be in fluid communication with said second sub-chamber 36, 36'. As it will be described in detail in the following of the present disclosure, in operation first 51, 51' and second 52, 52' outlet fluid pathways of outlet fluid circuit 50, 50' alternatively discharge the first fluid from first sub-chamber 35 and from second sub-chamber 36 as well as the second fluid from first sub-chamber 35' and from second sub-chamber 36'.

Downstream from first outlet port 53, 53', first outlet fluid pathway 51, 51' is provided with a first outlet fluid circuit valve 55, 55' which allows first and second fluids to being discharged respectively from first sub-chamber 35, 35' through first outlet fluid pathway 51, 51' and from second sub-chamber 36, 36' through second outlet fluid pathway 52, 52'. According to an embodiment of the present disclosure, first outlet fluid circuit valve 55, 55' is a check valve, i.e. a one-way valve which prevents reverse flow, thereby allowing the fluid to flow through it in only one direction, specifically exiting from first sub-chamber 35, 35', and avoiding that the fluid flows back into said first sub-chamber 35, 35'.

Analogously, downstream from second outlet port 54, 54', second outlet fluid pathway 52, 52' is provided with a second outlet fluid circuit valve 56, 56' which allows first and second fluids to being discharged, respectively, from second sub-chamber 36, 36' through second outlet fluid pathway 52, 52'. According to an embodiment of the present disclosure, second outlet fluid circuit valve 56, 56' is a check valve, i.e. a one-way valve which allows the fluid to flow through it in only one direction, specifically exiting from second sub-chamber 36, 36', thereby avoiding that the fluid flows back into said second sub-chamber 36, 36'.

Preferably, first 55, 55' and second 56, 56' outlet fluid circuit valves are spring loaded check valves wherein a spring component is used to support valve operation by eliminating the effect of gravity on the check valve function. More preferably, first 55, 55' and second 56, 56' outlet fluid circuit valves are spring loaded ball check valves.

According to the embodiment shown in FIG. 1, fluid delivery system 100 of the present disclosure further comprises a first recirculation fluid circuit 60 and a second recirculation fluid circuit 60', said recirculation fluid circuits being also indicated in the present description as additional fluid circuits (i.e. additional fluid circuits with respect to inlet and outlet fluid circuits mentioned above). In detail, first recirculation fluid circuit 60 fluidically connects first and second variable-volume sub-chambers 35, 36 of chamber 31 of first pump module 30, said first recirculation fluid circuit 60 cooperating with a first actuator 70 (possessed by said first recirculation fluid circuit 60) for managing the passage of the first fluid in both directions between said first and second variable-volume sub-chambers 35, 36. Analogously, second recirculation fluid circuit 60' fluidically connects first and second variable-volume sub-chambers 35', 36' of chamber 31' of second pump module 30', said second recirculation fluid circuit 60' cooperating with a second actuator 70' (possessed by said second recirculation fluid circuit 60') for managing the passage of the second fluid in both directions between said first and second variable-volume sub-chambers 35', 36'.

According to the embodiment shown in FIG. 1, first and second recirculation fluid circuits 60, 60' are external to chambers 31, 31' and they fluidically connect, respectively, separate branches of first and second inlet fluid circuits 40, 40' upstream from the inlet ports 44, 44' and 46, 46' of respective sub-chambers 35, 35' and 36, 36'. In detail, with reference to first pump module 30, a first axial end 61 of first recirculation fluid circuit 60 fluidically connects with second inlet fluid pathway 42 of first inlet fluid circuit 40 downstream from first inlet fluid circuit valve 45 thereof, while a second axial end 62 of first recirculation fluid circuit 60 fluidically connects with third inlet fluid pathway 43 of first inlet fluid circuit 40 downstream from second inlet fluid circuit valve 47 thereof. Analogously, with reference to second pump module 30', a first axial end 61' of second recirculation fluid circuit 60' fluidically connects with second inlet fluid pathway 42' of second inlet fluid circuit 40' downstream from first inlet fluid circuit valve 45' thereof, while a second axial end 62' of second recirculation fluid circuit 60' fluidically connects with third inlet fluid pathway 43' of second inlet fluid circuit 40' downstream from second inlet fluid circuit valve 47' thereof.

First and second actuators 70, 70' are active valves that are operated by fluid delivery system 100, as it will be explained in detail in the following of the present description. Preferably, first and second actuators 70, 70' are electro-mechanical driven valves that are automatically controlled and operated by a processor or control unit P of fluid delivery system 100. As schematically shown in the figures, processor P controls and operates first and second actuators 70, 70', driving unit M as well as first and second supply station valves 11, 11'.

Figure 2:
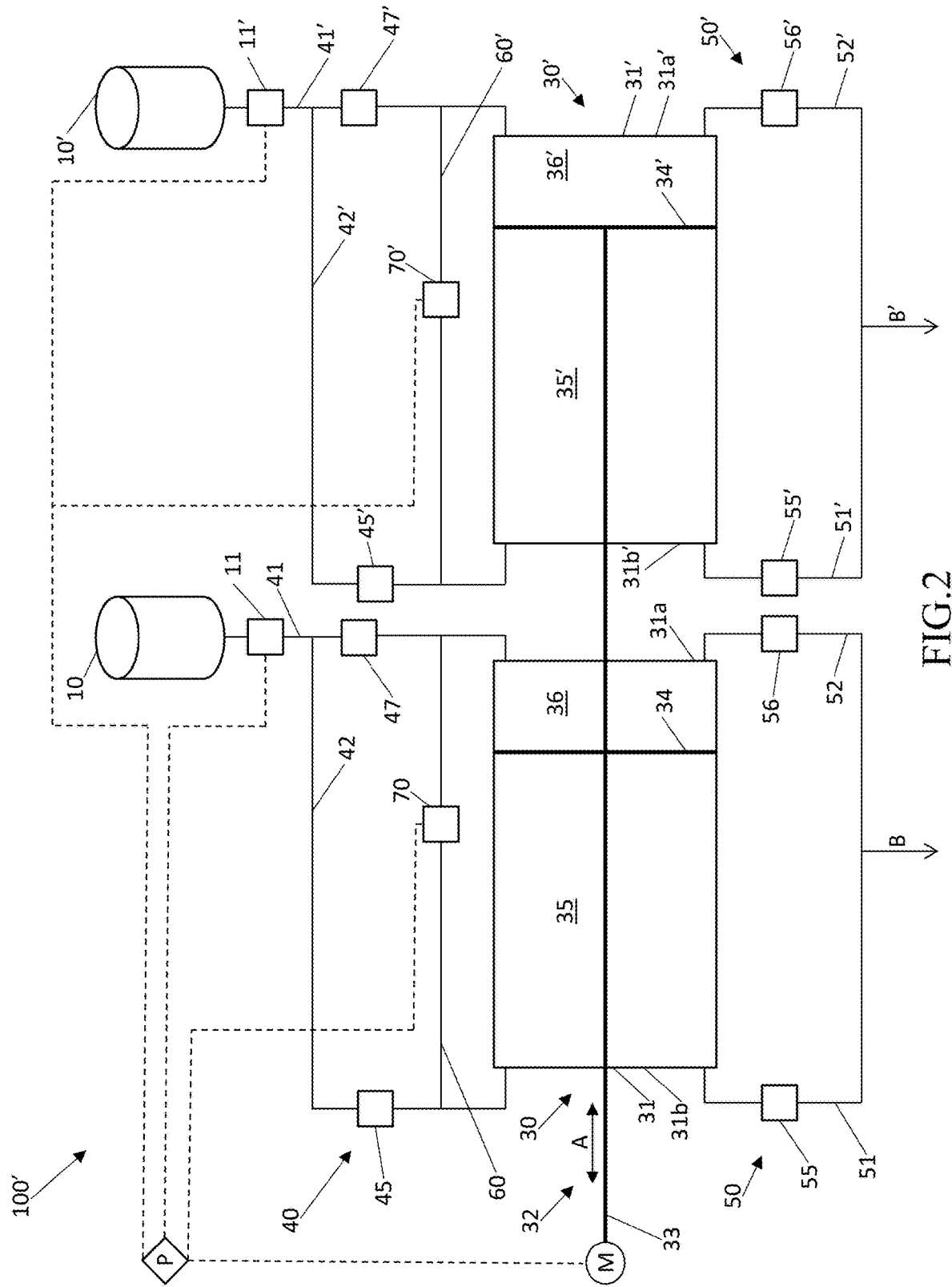
FIG. 2 shows a schematic representation of an alternative fluid delivery system of the present disclosure wherein two pump modules are arranged in series.

According to an alternative embodiment shown in FIG. 2, a fluid delivery system 100' is schematically represented in which said two pump modules 30, 30' are arranged in series and not in parallel as shown in the embodiment of FIG. 1. In this alternative embodiment the two chambers 31, 31' are separate and spaced apart from each other, while a common piston rod 33 with two spaced apart plungers 34, 34' is provided within said chambers 31, 31', thereby defining respective first 35, 35' and second 36, 36' variable-volume sub-chambers. All the remaining components (as well as functioning thereof) of said alternative embodiment are identical to respective components of fluid delivery system 100 shown in FIG. 1 and thus are indicated with same reference numbers.

Figure 3:
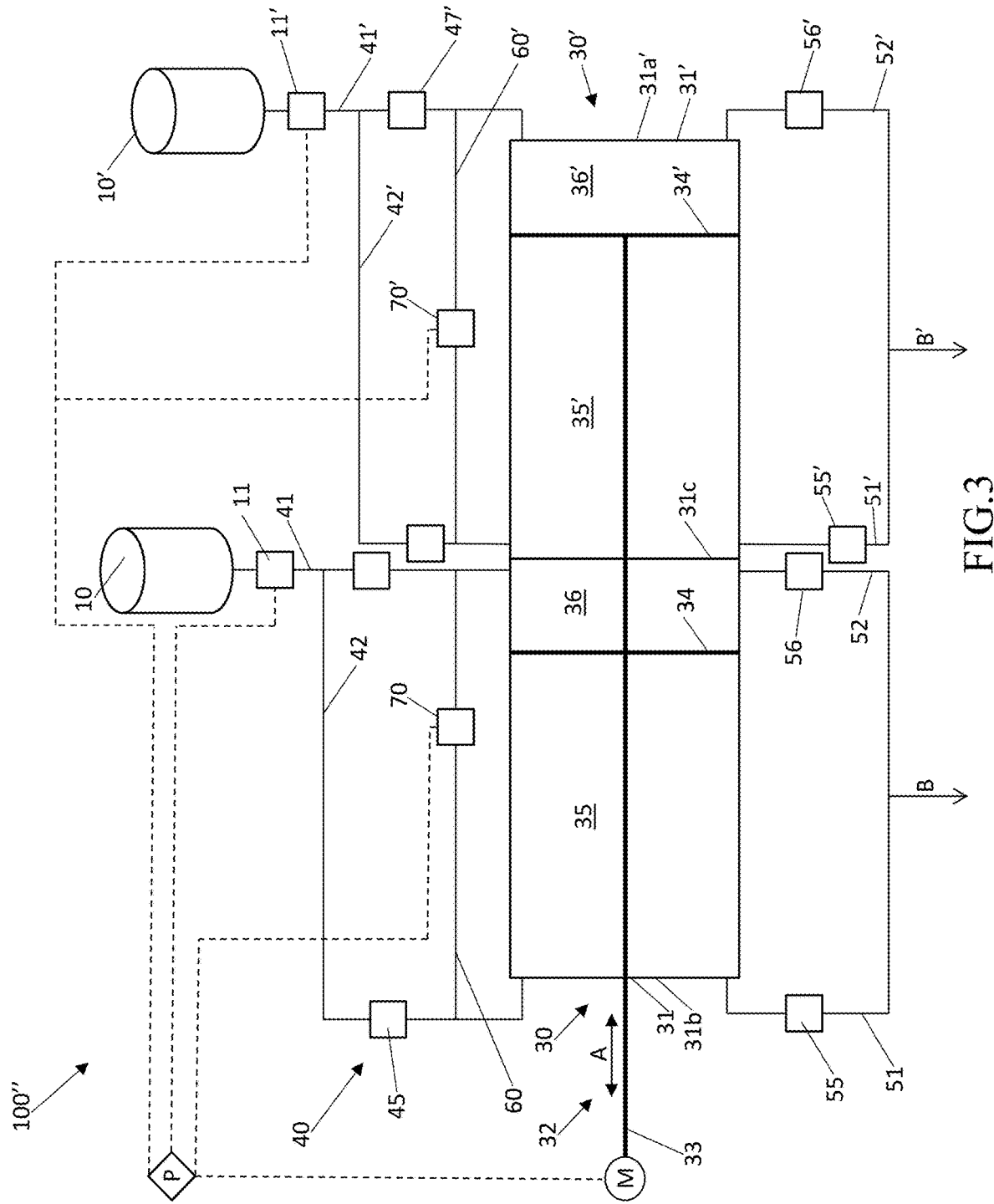
FIG. 3 shows a schematic representation of an alternative arrangement of the embodiment of FIG. 2.

An alternative arrangement to the embodiment of FIG. 2 is schematically represented in FIG. 3 according to which a fluid delivery system 100" comprises two pump modules 30, 30' that are arranged in parallel (analogously to the embodiment of FIG. 2), but with the two chambers 31, 31' sharing a common base wall 31c. In detail, the two chambers 31, 31' are consecutively arranged along their common longitudinal axis and adjacent to each other through said common base wall 31c. According to this embodiment a common piston rod 33 with two spaced apart plungers 34, 34' is provided within said chambers 31, 31', thereby defining respective first 35, 35' and second 36, 36' variable-volume sub-chambers. All the remaining components (as well as functioning thereof) of this alternative embodiment are identical to respective components of fluid delivery system 100' shown in FIG. 2 and thus are indicated with same reference numbers.

Figure 4:
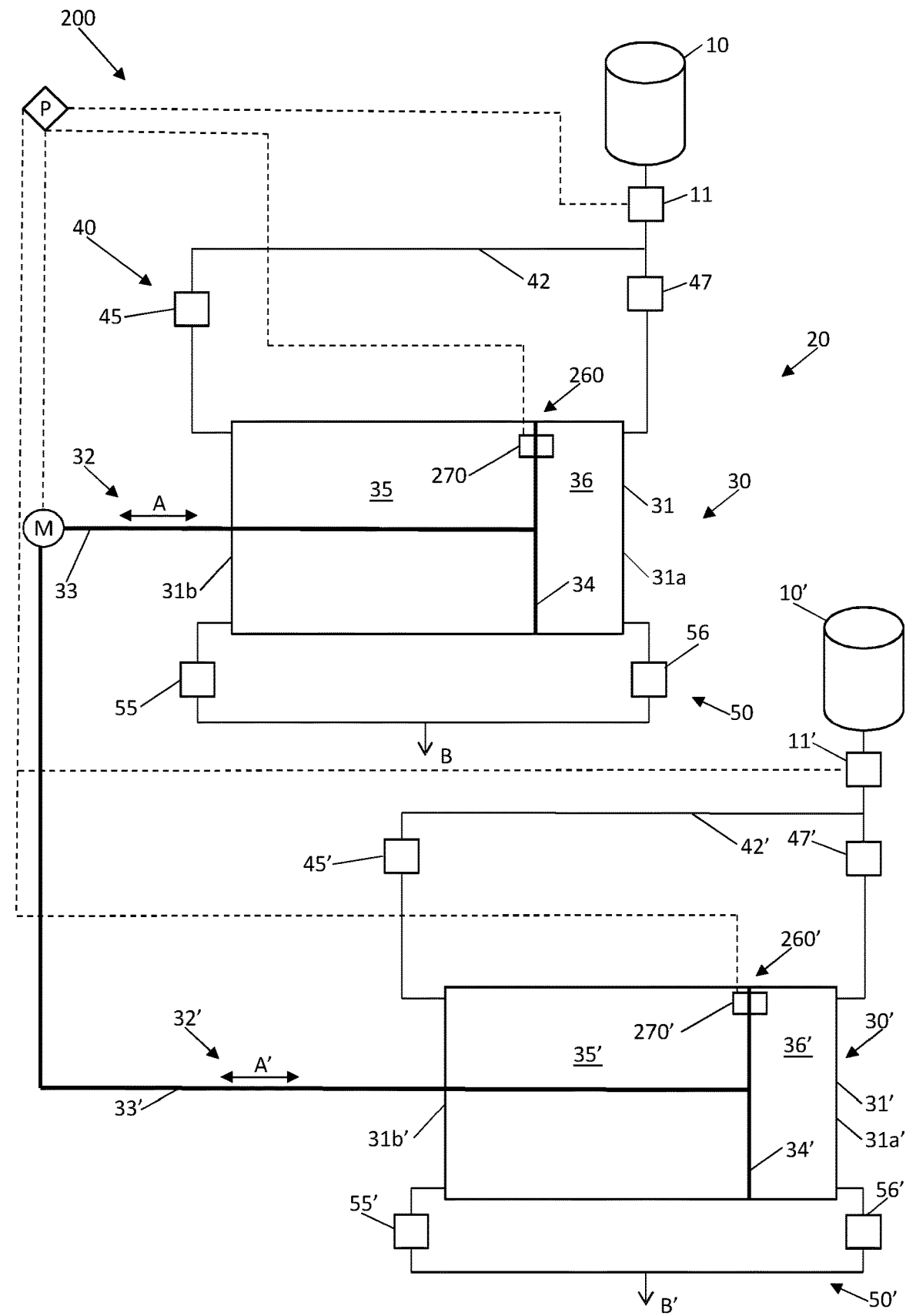
FIG. 4 shows a schematic representation of an alternative solution of the embodiment of FIG. 1.

According to an alternative embodiment shown in FIG. 4, a fluid delivery system 200 comprises, for each pump module 30, 30' thereof, a recirculation circuit 260, 260' and an actuator 270, 270' which are located inside respective chamber 31, 31'. In particular, recirculation circuit 260, 260' and actuator 270, 270' are integral with plunger 34, 34' of piston 32, 32', i.e. the recirculation circuit and the actuator are integrated in the plunger component. In more detail, recirculation circuit 260, 260' comprises a fluid passage obtained within the plunger thickness for ensuring fluid communication between sub-chambers 35, 36 and 35', 36', respectively. In other words, recirculation circuit 260, 260' is a duct (through hole) provided within the plunger, the diameter (radial extension) of said duct being remarkably lower than the plunger extension (length). According to said alternative embodiment shown in FIG. 4, actuator 270, 270' is arranged inside recirculation circuit 260, 260' and it is automatically controlled and operated by processor P of fluid delivery system 200. Again, all the remaining components of this alternative embodiment (as well as functioning thereof) are identical to respective components of fluid delivery system 100 shown in FIG. 1 and thus are indicated with same reference numbers.

Figure 5:
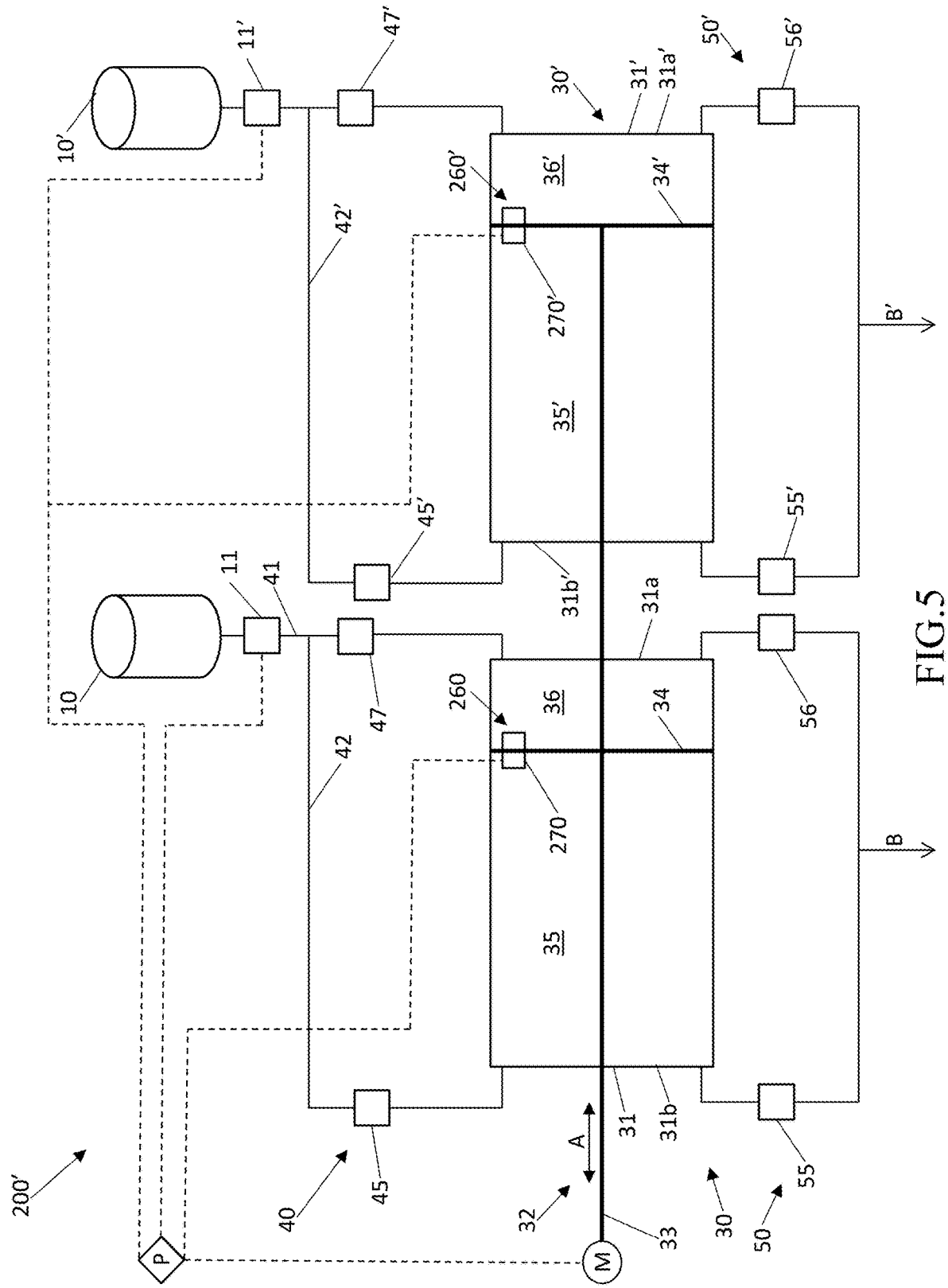
FIG. 5 shows a schematic representation of an alternative solution of the embodiment of FIG. 2.

According to an alternative embodiment shown in FIG. 5, fluid delivery system 200' combines the main technical features of fluid delivery system 100' represented in FIG. 2 with the main technical features of fluid delivery system 200 represented in FIG. 4. In detail, fluid delivery system 200' comprises two pump modules 30, 30' arranged in series (with respective chambers 31, 31' spaced apart from each other) and each pump module 30, 30' is provided with recirculation circuit 260, 260' and actuator 270, 270' that are located inside said respective chamber 31, 31'. The configuration shown in FIG. 5 is also applicable to a fluid delivery system (not indicated in the figures) that combines the main technical features of fluid delivery system 100" represented in FIG. 3 (wherein the two chambers 31, 31' are consecutively arranged along their common longitudinal axis and adjacent to each other through common base wall 31c) with the main technical features of fluid delivery system 200 of FIG. 5.

Figure 6:
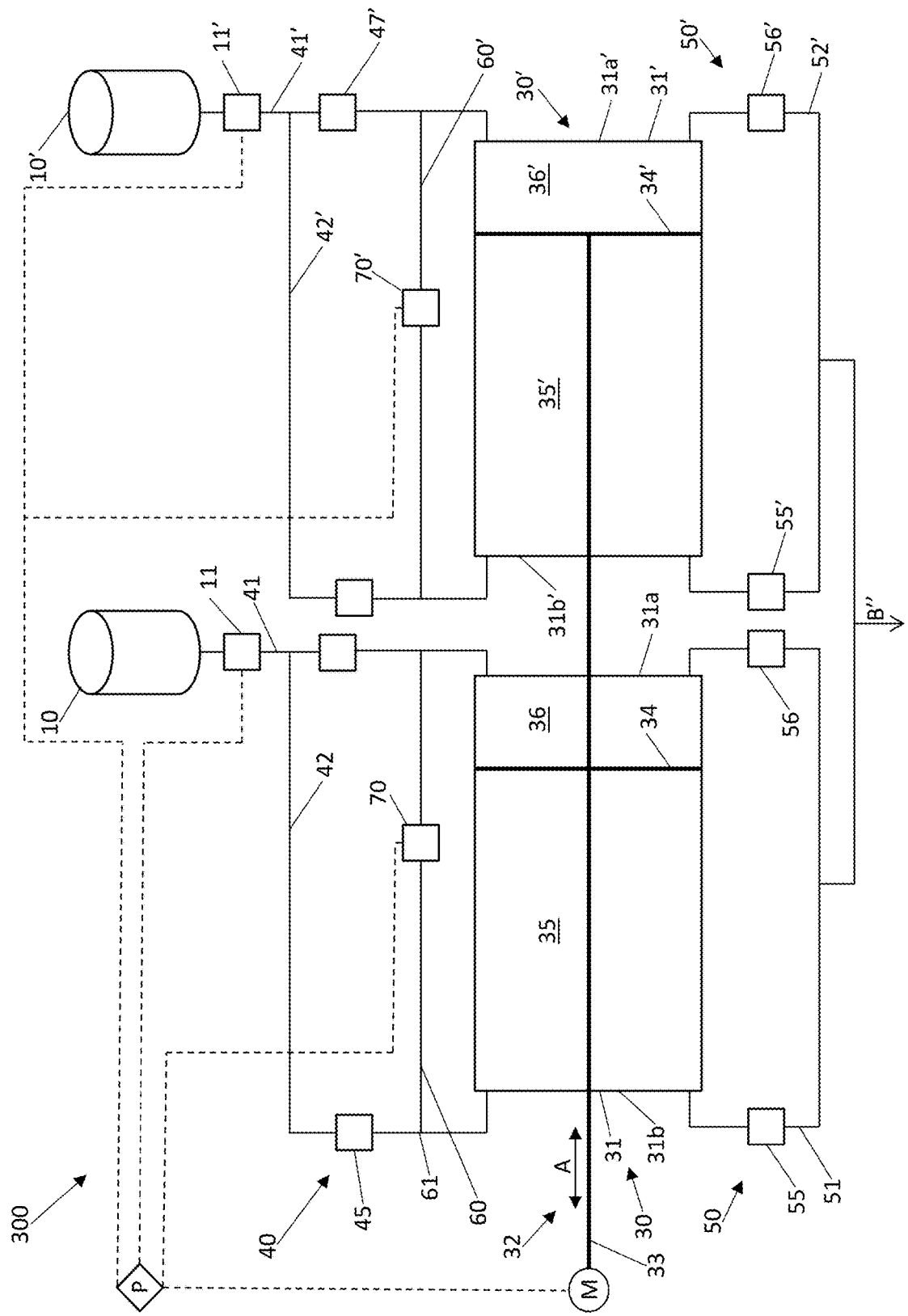
FIG. 6 shows a schematic representation of an alternative solution of the embodiment of FIG. 2.

According to an alternative embodiment shown in FIG. 6, first outlet fluid circuit 50 and second outlet fluid circuit 50' of fluid delivery system 300 have a common output (see arrow B''') for delivering the first fluid (exiting from first pump module 30) and the second fluid (exiting from second pump module 30'). This technical solution is particularly advantageous, for instance, in case the first and the second fluid are requested to be mixed exactly before being delivered (e.g. first and second fluids are the components of a given glue or coating formulation, and they should not be mixed in advance, but should be combined immediately before delivery thereof and their successive application). All the remaining components of this alternative embodiment (as well as functioning thereof) are identical to respective components of fluid delivery system 100' shown in FIG. 2 and thus are indicated with same reference numbers According to an alternative embodiment shown in FIG. 7, pressurizing unit 20 of fluid delivery system 400 comprises two separate driving units M, M' so that each pump module 30, 30' is operated by a respective dedicated driving unit (i.e. driving unit M is acting on piston 32 of first pump module 30, and driving unit M' is acting on piston 32' of second pump module 30'). Operation of the fluid delivery system according to this embodiment is particularly efficient in terms of fluid flow control as well as of delivery accuracy of the desired fluid volume. In fact, a fluid delivery system comprising one single driving unit necessarily displaces the sub-chambers variable volumes within the two chambers 31, 31' at the same flow rate. In some applications this aspect is difficult to be managed and regulated, for example when mixing of two fluids (a first fluid processed by first pump module 30 and a second fluid processed by second pump module 30', said first fluid being different from said second fluid) is desired, especially if mixing is requested to be different than a 50/50% mixing ratio (i.e. 50% of the first fluid and 50% of the second fluid). For instance, in case a 30/70% mixing ratio is requested to be delivered by fluid delivery system 400 (i.e. a mixture of 30% of the first fluid and 70% of the second fluid), actuators 70, 70' of respective first and second recirculation fluid circuits 60, 60' are closed and the speeds of pistons 32, 32' can be set to different values from each other (fact which is made possible since each piston is independently operated by a separate, independent driving unit) in order to properly achieve the desired 30/70% mixing ratio. It can be underlined that, also for the embodiment in which the fluid delivery system comprises two separate driving units, it is particularly advantageous to provide the two pump modules with their respective recirculation fluid circuits because said circuits ensure proper and continuous recirculation of each single fluid within its respective pump module (i.e. the first fluid is continuously recirculated within first pump module 30 and the second fluid is continuously recirculated within second pump module 30'), said predetermined recirculation contributing in keeping moving, and thus keeping mixed and shaken, the fluids (i.e. each single fluid) before delivery thereof.

Figure 8:
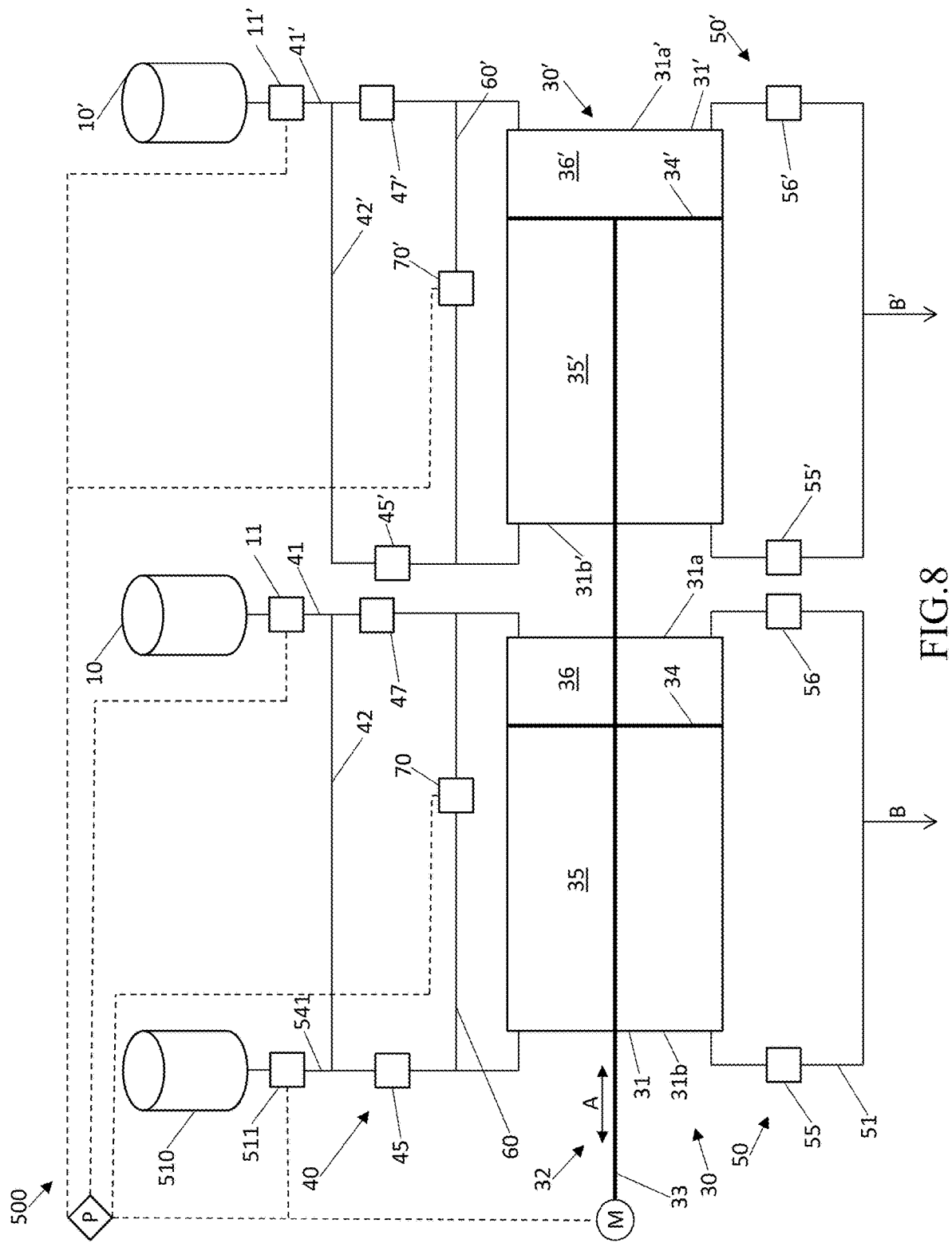
FIG. 8 shows a schematic representation of an alternative solution of the embodiment of FIG. 2.

According to a further alternative embodiment shown in FIG. 8, fluid delivery system 500 comprises a first additional supply station 510 in fluid communication with first pump module 30. Analogously to the embodiment shown in FIG. 2, first inlet fluid circuit 40 comprises an additional first inlet fluid pathway 541 which fluidically connects first additional supply station 510 to second inlet fluid pathway 42 of first inlet fluid circuit 40. Moreover, said additional first inlet fluid pathway 541 comprises an additional supply station valve 511 that allows the fluid to be discharged from first additional supply station 510. Additional supply station valve 511 is an active valve that is operated by fluid delivery system 500, as it will be explained in detail in the following of the present description.

According to a further embodiment (not shown in the figures), fluid delivery system 500 comprises a second additional supply station in fluid communication with second pump module 30'.

According to a further embodiment (not shown in the figures), first additional supply station 510 in fluid communication with first pump module 30 and/or second additional supply station in fluid communication with second pump module 30' are/is provided to any of the disclosed embodiments of a fluid delivery system according to the present disclosure (e.g. to fluid delivery system 100 of FIG. 1, fluid delivery system 100'' of FIG. 3, fluid delivery system 200 of FIG. 4, fluid delivery system 200' of FIG. 5, fluid delivery system 300 of FIG. 6).

In a first embodiment, the additional supply station fluidically connected to a given pump module contains the same fluid stored in the supply station of said pump module. Therefore, this additional supply station is envisaged either to provide the fluid delivery system with a back-up solution in case of malfunction of the supply station, or to provide a fluid supplemental source for increasing autonomy of the fluid delivery system as well as for ensuring fluid delivery continuity when the supply station is running out of fluid.

In a second embodiment, the additional supply station fluidically connected to a given pump module contains a fluid different from the fluid contained in the supply station of said pump module. For instance, the fluid contained in the supply station is a contrast agent at high concentration (e.g. ISOVUE®-370) while the fluid contained in the additional supply station is a saline solution. This solution is particularly advantageous since, by suitably mixing the high concentrated contrast agent with the saline solution, the fluid delivery system would be able to provide volumes of contrast agent at different concentrations by starting from one single type of high concentrated contrast agent. The mixing step for reaching the contrast agent desired concentration to be delivered for a given patient and/or for a given medical (diagnostic or therapeutic) application will be described in detail in the following of the present description.

Operation of the delivery system according to the present disclosure will be illustrated in the following with reference to some embodiments described above and with reference to applications related to the medical field, more specifically to alternate or simultaneous injection of a contrast agent and a saline solution for diagnostic purposes. However, as already mentioned above in the present description, a delivery system according to the present disclosure can be used in other technological areas not correlated to medical/healthcare applications. Moreover, the general operational principles—that will be illustrated herein below with reference to some embodiments of the delivery system of the present disclosure—are applicable to the plurality of embodiments disclosed in the present description and/or shown in the figures correlated thereto.

Figure 9:
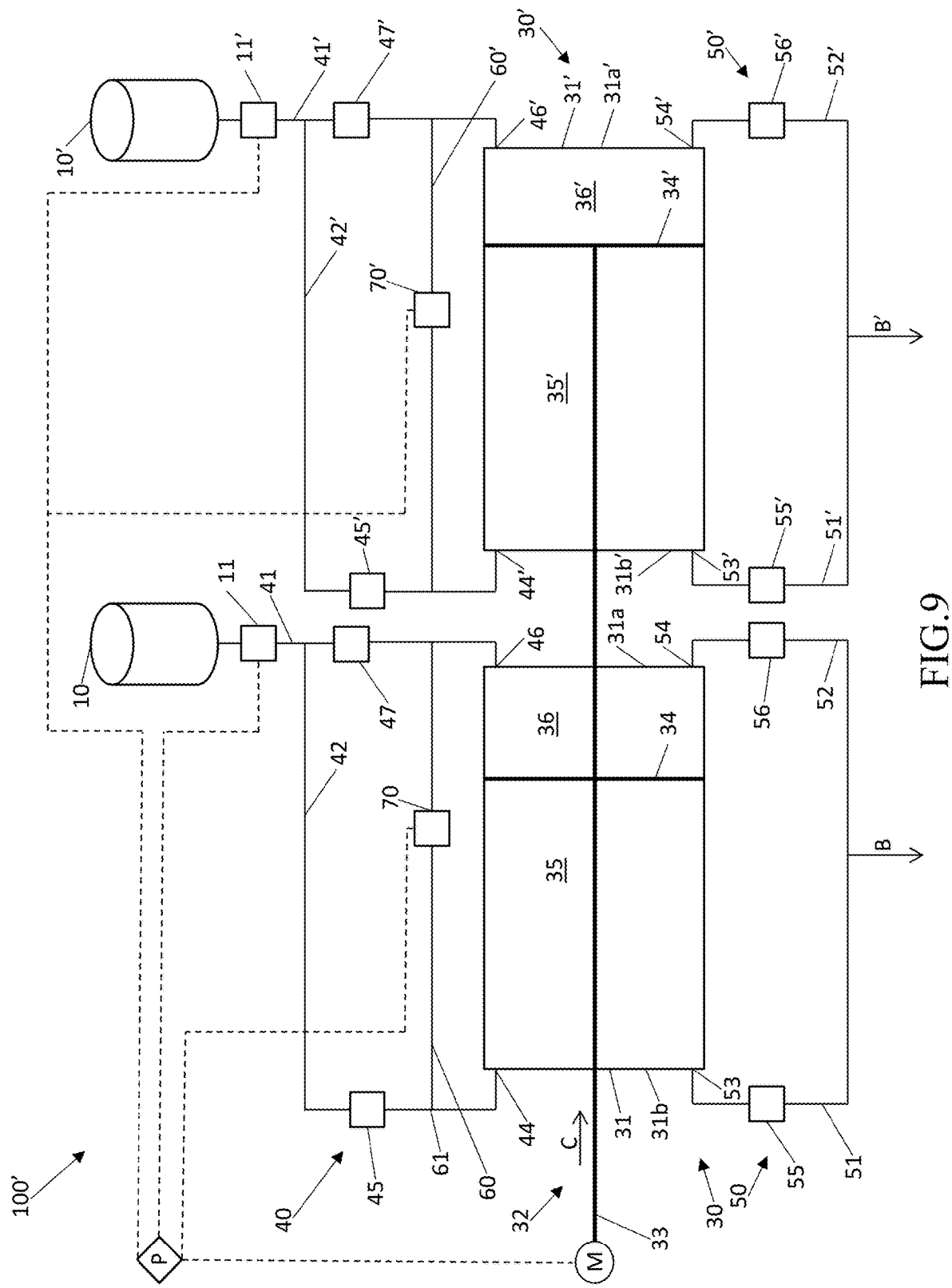
FIG. 9 to FIG. 10 show a schematic representation of the operation steps of the fluid delivery system shown in FIG. 2.
Figure 10:
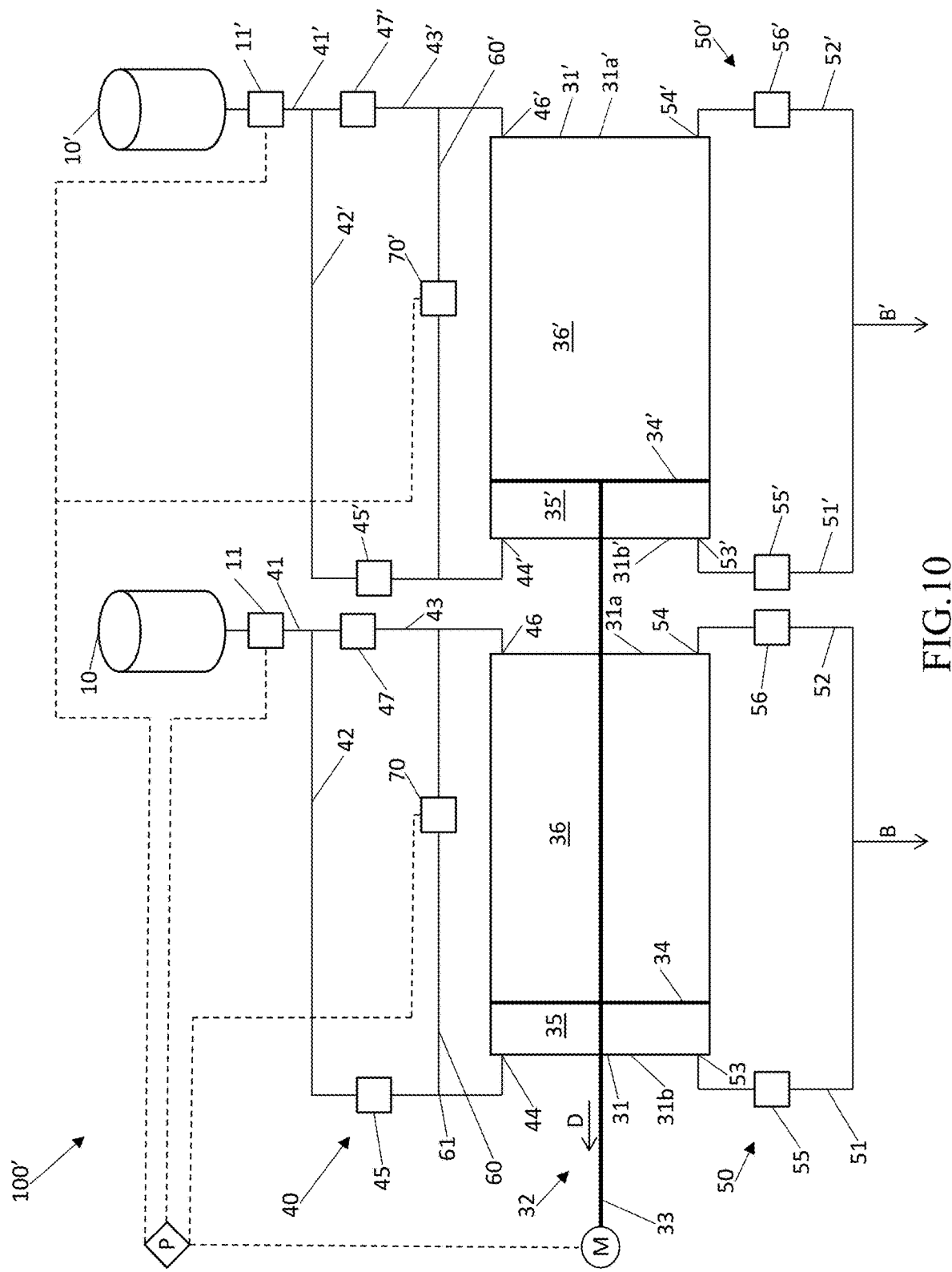

As a first example of a method of operating a delivery system according to the present disclosure, reference is made to FIG. 9 and FIG. 10 in which delivery system 100' according to the embodiment shown in FIG. 2 is exemplified.

Supply station 10 contains a first fluid (not shown), for instance a contrast agent, which is requested to be injected to a patient by delivery system 100' (see arrow B), while supply station 10' contains a second fluid (not shown), for instance a saline solution, which is requested to be injected to the patient by said delivery system 100' (see arrow B'). Typically, first fluid exiting at B and second fluid exiting at B' are conveyed to the patient through a common tubing (patient line—not shown) which is mechanically and fluidically connected to a catheter and/or a needle for accessing patient's vasculature.

As a first initiation step, the method of delivery according to the present disclosure comprises the step of filling first and second sub-chambers 35, 36 of first pump module 30 with the first fluid and, analogously, the step of filling first and second sub-chambers 35', 36' of second pump module 30' with the second fluid. In order to perform said filling steps, processor P opens supply station valves 11, 11', it closes actuators 70, 70' of first and second recirculation fluid circuits 60, 60' and it acts on driving unit M for reciprocating common piston 32 within chambers 31, 31', thereby allowing the first and the second fluids to exit supply stations 10, 10' respectively, and to flow through first inlet fluid circuit 40 and through second inlet fluid circuit 40'. In detail, as soon as piston 32 is axially translated along a first direction (e.g. arrow C of FIG. 9), under-pressure is generated in the first sub-chambers (e.g. sub-chambers 35, 35') which are increasing their volume due to the piston axial movement. Therefore, the respective fluids are allowed to flow through first 41, 41' and second 42, 42' inlet fluid pathways of first and second inlet fluid circuits 40, 40', through the corresponding first inlet fluid circuit valves (e.g. first inlet fluid circuit valves 45, 45'), and then they enter and fill said first sub-chambers. At the same time, the air contained within the second sub-chambers (e.g. sub-chambers 36, 36')—which are decreasing their volume due to the piston axial movement (arrow C)—is primed away from the fluid delivery system through venting means possessed by the opposite second inlet fluid circuit valves (e.g. second inlet fluid circuit valves 47, 47'). In fact, the air contained in said first sub-chambers 35, 35' is generally forced to exit said sub-chambers by passing through first inlet ports 44, 44', then through second inlet fluid pathways 42, 42' and finally through said first inlet fluid circuit valves 45, 45'. Successively, in order to fill the second sub-chambers with the respective fluids and to prime the first sub-chambers (i.e. expelling air therefrom), processor P acts on driving unit M for inverting the piston movement so that the piston is axially translated along a second direction opposite to the first direction (e.g. arrow D of FIG. 10). Since actuators 70, 70' are kept closed while the piston is moving during the filling and priming steps, under-pressure is generated in the second sub-chambers (e.g. sub-chambers 36, 36') which are increasing their volume due to the piston axial movement (arrow D). Therefore, the first and second fluids are allowed to flow through first 41, 41' and third 43, 43' inlet fluid pathways of first and second inlet fluid circuits 40, 40' respectively, through the corresponding second inlet fluid circuit valves (e.g. second inlet fluid circuit valves 47, 47'), and then they enter and fill said second sub-chambers. At the same time, the air still contained within the first sub-chambers (e.g. sub-chambers 35, 35')—which are decreasing their volume due to the piston axial movement (arrow D)—is primed away from the fluid delivery system through venting means possessed by the corresponding first inlet fluid circuit valves (e.g. first inlet fluid circuit valves 45, 45'). In fact, the air contained in said second sub-chambers 36, 36' is generally forced to exit said sub-chambers by passing through second inlet ports 46, 46', then through third inlet fluid pathways 43, 43' and finally through second inlet fluid circuit valves 47, 47'. During the priming steps some amounts of the first fluid and of the second fluid exit from the fluid delivery system through first 50 and second 50' outlet fluid circuits, so that priming of also said first 50 and second 50' outlet fluid circuits can be suitably performed.

Alternatively, air priming of the fluid delivery system is performed by dedicated venting means (not shown in the drawings) which is separate from the fluid circuit valves. According to an alternative embodiment, a dedicated venting means is associated with each valve of the fluid delivery system. According to a further alternative embodiment, a dedicated venting means is associated with each actuator 70, 70' of first and second recirculation fluid circuits 60, 60'.

As soon as chambers 31, 31' are filled up with the first fluid and the second fluid, respectively, and priming of the fluid delivery system is completed, processor P closes supply station valves 11, 11' and it opens actuators 70, 70' of first and second recirculation fluid circuits 60, 60', while driving unit M is still operated, thereby keeping piston 32 axially translating (arrows C and D) within chambers 31, 31'. Alternatively, processor P opens actuators 70, 70' of first and second recirculation fluid circuits 60, 60' while supply station valves 11, 11' are kept in their open working state when the two fluids are recirculated inside their respective chambers 31, 31'.

By keeping actuators 70, 70' of first and second recirculation fluid circuits 60, 60' in their open working state, fluid delivery system 100' is prevented from delivering the first and the second fluids outside thereof. In fact, thanks to the open working state of actuators 70, 70' and to the axial translation of piston 32, the first fluid is continuously recirculated within first chamber 31 through first recirculation fluid circuit 60, while the second fluid is continuously recirculated within second chamber 31' through second recirculation fluid circuit 60'. In detail, when piston 32 is moved in a first direction (e.g. arrow C of FIG. 9), the first fluid contained in second sub-chamber 36 is pushed through second inlet port 46 thereof and then through first recirculation fluid circuit 60 and through first actuator 70 to enter first sub-chamber 35 at first inlet port 44. At the same time, the second fluid contained in second sub-chamber 36' is pushed through second inlet port 46' thereof and then through second recirculation fluid circuit 60' and through second actuator 70' to enter first sub-chamber 35' at first inlet port 44'.

Thereafter, when piston 32 has reached its first end-stop, i.e. plunger 34 has completed its axial translation in said first direction (right direction of FIG. 9—see arrow C) and it has arrived in proximity of base wall 31*a* of chamber 31 and, simultaneously, plunger 34' has arrived in proximity of base wall 31*a*' of chamber 31', processor P acts on driving unit M to reverse piston axial translation (left direction of FIG. 10—see arrow D). Analogously to the piston first run described above, the first fluid contained in first sub-chamber 35 is pushed through first inlet port 44 and then through first recirculation fluid circuit 60 and through first actuator 70 to enter second sub-chamber 36 at second inlet port 46. At the same time, the second fluid contained in first sub-chamber 35' is pushed through first inlet port 44' and then through second recirculation fluid circuit 60' and through second actuator 70' to enter second sub-chamber 36' at second inlet port 46'.

Then, as soon as piston 32 has reached its second end-stop, i.e. plungers 34, 34' have completed their axial translations in the second direction (left direction in FIG. 10—see arrow D) and they arrive in proximity of base walls 31*b*, 31*b*' of respective chambers 31, 31' (so that first sub-chambers 35, 35' contain a substantially small volume of respective fluids while second sub-chamber 36, 36' contain a large volume of respective fluids), processor P acts on driving unit M to reverse again piston axial translation (right direction in FIG. 9—see arrow C), thereby starting a new charge/discharge cycle of chambers 31, 31' of fluid delivery system 100'. Of course, any number of cycles can be arranged for, said number depending on the requirements of the specific fluids to be delivered and on the specific application in which the fluid delivery system is implemented. As already mentioned above, said initial recirculating steps of the two fluids within their respective chambers are particularly advantageous since they allow keeping the two fluids moving within the fluid delivery system, thereby ensuring proper and homogeneous shaking of each single fluid before delivery thereof.

It has to be pointed out that the fluids contained in second sub-chambers 36, 36' and pushed by plungers 34, 34' are allowed neither to flowing back into supply stations 10, 10' nor to accessing second outlet fluid pathways 52, 52' of first and second outlet fluid circuits 50, 50'. In fact, preferably supply station valves 11, 11' are closed and, moreover, both first 45, 45' and second 47, 47' inlet fluid circuit valves are one-way valves which allow the fluids flowing from supply stations 10, 10' into respective chambers 31, 31', but not vice versa, thereby avoiding the fluids discharged from first 35, 35' and second 36, 36' sub-chambers to flowing back through first 41, 41' and second 42, 42' inlet fluid pathways of first and second inlet fluid circuits 40, 40'. Moreover, since first 55, 55' and second 56, 56' outlet fluid circuit valves automatically open only when the fluids discharged respectively from first 35, 35' and second 36, 36' sub-chamber have a sufficiently high pressure for overcoming the internal resilience of said valves (preferably, first and second outlet fluid circuit valves are ball spring-loaded check valves), when actuators 70, 70' are in the open state the fluids discharged from first 35, 35' and second 36, 36' sub-chambers do not have enough force to overcome the internal resilience of first 55, 55' and second 56, 56' outlet fluid circuit valves, and thus the fluids are not delivered outside of fluid delivery system 100', but they are recirculated inside their respective sub-chambers.

It is apparent from the above that the fluid delivery system of the present disclosure allows a continuous and predefined movement (e.g. in terms of volumes, piston translational speed) of one fluid or of both fluids before exiting the fluid delivery system. As already mentioned above, this aspect of the present disclosure is particularly advantageous in case a specific fluid property (e.g. composition homogeneity, temperature, viscosity, mixture, fluidity) is requested to be achieved and/or maintained before starting delivery of that fluid. In fact, the fluid delivery system according to the present disclosure allows the fluids introduced into first 31 and second 31' chambers to be continuously recirculated by being alternately charged/discharged between first 35, 35' and second 36, 36' sub-chambers when fluid delivery system 100' is not delivering, i.e. the fluids are not definitely exiting the fluid delivery system. Thanks to first 60 and second 60' recirculation fluid circuits, and first 70 and second 70' actuators associated thereto, recirculation of the fluids and redistribution thereof between the two sub-chambers contributes in balancing the pressure therein. This aspect is particularly advantageous since it allows to operate the system at a limited (low) pressure, at least in the initial stage when the delivery system is not yet delivering the fluids outside the system, thereby limiting the technical constraints which would need to be implemented if the system were required to operate at higher pressure values.

As soon as recirculation is completed (e.g. the desired homogeneity of one fluid or of both fluids is successfully reached and, at a certain point in time, the delivery of the first fluid and/or of the second fluid is requested to be started), processor P suitably acts on first or second actuators 70, 70' to close it/them and to stop the recirculation step of at least one of said first and second fluids.

For example, in case the first fluid contained within supply station 10 is requested to be delivered first, processor P closes first actuator 70 of first recirculation fluid circuit 60, while second actuator 70' of second recirculation fluid circuit 60' is still kept in its open working condition so that delivery (arrow B) of the first fluid can be performed while the second fluid is kept recirculating inside its respective chamber 31'. This is the case, for instance, in which at a given time of an injection/infusion process performed on a given patient undergoing an examination procedure (e.g. a CT diagnostic examination), fluid delivery system 100' is requested to deliver only the first fluid (e.g. contrast agent) contained within supply station 10, while recirculation of the second fluid (e.g. saline solution) is performed (i.e. the second fluid is not delivered outside of the fluid delivery system at that moment in time).

Therefore, the method of delivery according to the present disclosure comprises the step of starting delivery (i.e. delivery outside of the fluid delivery system) of the first fluid contained within first chamber 31. In order to perform said step, as mentioned above processor P closes first actuator 70 of first recirculation fluid circuit 60 and it opens first supply station valve 11. During delivery of the first fluid (fluid exiting the fluid delivery system—see arrow B), first supply station valve 11 is maintained in its open state because it is important to refill sub-chambers 35, 36 of first chamber 31 with new first fluid in order to avoid fluidic perturbations possibly impacting on the correct functioning of the piston and, consequently, of the overall fluid delivery system. Since closing first actuator 70 prevents first fluid from flowing through first recirculation fluid circuit 60 (while, as already mentioned above, first and second inlet fluid circuit valves 45, 47 do not allow any flow back of the first fluid towards first supply station 10), pushing first plunger 34 in the first direction (arrow C of FIG. 9) and then in the second opposite direction (arrow D of FIG. 10) allows the first fluid to exit, respectively, second outlet port 54 and first outlet port 53 of first chamber 31. Therefore, when the first fluid is pushed to pass through second outlet port 54 (arrow C), the first fluid flows into second outlet fluid pathway 52 of first outlet fluid circuit 50 and then it passes through second outlet fluid circuit valve 56 because at this stage of the procedure, since first actuator 70 is closed, the fluid pressure is sufficiently high to overcome the internal resilience of said second outlet fluid circuit valve 56. Analogously, when the first fluid is pushed to pass through first outlet port 53 (arrow D), the first fluid flows into first outlet fluid pathway 51 of first outlet fluid circuit 50 and then it passes through first outlet fluid circuit valve 55 because at this stage of the procedure, since first actuator 70 is closed, the fluid pressure is sufficiently high to overcome the internal resilience of said first outlet fluid circuit valve 55. Consequently, the first fluid is finally delivered (arrow B) by sequentially discharging it from first and second sub-chambers 35, 36 of first chamber 31. In fact, since first and second outlet fluid circuit valves 55, 56 are one-way valves, the first fluid cannot flow back through the under-pressurized pathway and thus it is necessarily forced to be delivered (arrow B).

It can be pointed out that the method of delivery according to the present disclosure does not necessarily require that sub-chambers 35, 36 are fully filled with the first fluid or that they are fully discharged of the first fluid. In other words, it is not mandatory that, during its back and forth axial translations, first plunger 34 reaches base walls 31a, 31b of first chamber 31. This means that the method of delivery according to the present disclosure can comprise partial charging/discharging steps of the first fluid into/from the respective sub-chambers of the first chamber, especially in case a defined (and typically small) volume of first fluid is requested to be delivered in one shot (i.e. along a single translational movement of the first plunger without reversing thereof). Of course, this aspect mentioned above can analogously apply also to sub-chambers 35', 36' of second chamber 31'.

As mentioned above, during the step of delivering the first fluid (arrow B), first supply station valve 11 is kept open so that new first fluid can alternately enter the two sub-chambers of the first chamber and undesired perturbations effects would not occur while the piston is axially translating within said first chamber 31. Even though the new first fluid entering the system during the step of delivering has not passed through first actuator 70 and first recirculation fluid circuit 60, it can be noted that the new first fluid is not instantly delivered. In fact, the new first fluid enters the under-pressurized sub-chamber, while the first fluid that is delivered by the system is the one contained in the pressurized sub-chamber. Therefore, before being delivered, the new first fluid is permanently moving and mixing within the respective sub-chamber thanks to the piston axial translation, thereby ensuring that the desired delivery conditions are reached before finally exiting the system.

As already mentioned above, the Applicant has found that recirculation of the first fluid within first chamber 31, by letting the first fluid flowing through first recirculation fluid circuit 60 and first actuator 70 associated thereto, can remarkably reduce or even completely remove the risk of pressure pulsations when the first fluid is being delivered, especially at the beginning of the fluid delivery procedure. Indeed, the fluid delivery system according to the present disclosure can properly control pressure drops or pressure spikes, occurring when piston 32 starts moving, thanks to the presence of first recirculation fluid circuit 60 and first actuator 70. In fact, according to the present disclosure, the fluid delivery system starts delivering the first fluid (outside of the fluid delivery system—arrow B) when recirculation of the first fluid inside first chamber 31 has already begun, therefore delivery will start when the piston is already moving inside first chamber 31. This clearly means that the start of fluid delivery is not simultaneous with the start of piston movement since delivery of the first fluid is started when the piston is already axially translating within first chamber 31 for allowing the first fluid recirculation step to be performed.

Furthermore, as already mentioned above, the Applicant has also found that recirculation of the first fluid within first chamber 31, by letting the first fluid flowing through first recirculation fluid circuit 60 and first actuator 70 associated thereto, can remarkably reduce or even completely eliminate the latency time of the fluid delivery system. The latency time is the technical time which the fluid delivery system inevitably requires in order to be ready to deliver the fluid. In fact, as soon as processor P instructs to deliver electric current to driving unit M, typically said electric current builds up an electromagnetic field which acts on rotor magnets that generate a torque on the gears, thereby causing the piston to start its movement. When the piston starts moving, fluid pressure starts building up and it still needs some additional time to reach and overcome the pressure threshold value which is set up for first and second outlet fluid circuit valves 55, 56. The sum of all these times is called "latency time" and it is far from being negligible, thereby inevitably causing a delay in fluid delivery out of the fluid delivery system. Thanks to the presence of first recirculation fluid circuit 60 and first actuator 70 associated thereto, fluid delivery system 100' of the present disclosure can overcome or reduce said latency time since, in order to perform recirculation of the first fluid within first chamber 31, piston 32 starts moving well in advance to fluid delivery. Therefore, as soon as processor P closes first actuator 70 for starting delivery of the first fluid (arrow B), the fluid pressure immediately increases and very quickly overcomes the pressure threshold value which is set up for first and second outlet fluid circuit valves 55, 56. Consequently, the first fluid is delivered by the system very soon after processor P has ordered to start delivering.

As soon as delivery of the first fluid (e.g. contrast agent) contained within first supply station 10 is requested to be terminated and delivery of the second fluid (e.g. saline solution) contained within second supply station 10' is requested to be started, processor P opens first actuator 70 of first recirculation fluid circuit 60 and it closes second actuator 70' of second recirculation fluid circuit 60' so that delivery (arrow B') of the second fluid is performed while the first fluid is recirculated inside its respective chamber 31.

Therefore, the method of delivery according to the present disclosure further comprises the step of starting delivery (i.e. delivery outside of the fluid delivery system) of the second fluid contained within first chamber 31'. In order to perform said step, as mentioned above processor P closes second actuator 70' of second recirculation fluid circuit 60' and it opens second supply station valve 11'. During delivery of the second fluid (fluid exiting the fluid delivery system—see arrow B'), second supply station valve 11' is maintained in its open state because it is important to refill sub-chambers 35', 36' of second chamber 31' with new second fluid in order to avoid fluidic perturbations possibly impacting on the correct functioning of the piston and, consequently, of the overall fluid delivery system. Since closing second actuator 70' prevents second fluid from flowing through second recirculation fluid circuit 60' (while, as already mentioned above, first and second inlet fluid circuit valves 45', 47' do not allow any flow back of the second fluid towards second supply station 10'), pushing second plunger 34' in the first direction (arrow C of FIG. 9) and in the second opposite direction (arrow D of FIG. 10) allows the second fluid to exiting, respectively, second outlet port 54' and first outlet port 53' of second chamber 31'. Therefore, when the second fluid is pushed to pass through second outlet port 54' (arrow C), the second fluid flows into second outlet fluid pathway 52' of second outlet fluid circuit 50' and then it passes through second outlet fluid circuit valve 56' because at this stage of the procedure, since second actuator 70' is closed, the fluid pressure is sufficiently high to overcome the internal resilience of said second outlet fluid circuit valve 56'. Analogously, when the second fluid is pushed to pass through first outlet port 53' (arrow D), the second fluid flows into first outlet fluid pathway 51' of second outlet fluid circuit 50' and then it passes through first outlet fluid circuit valve 55' because at this stage of the procedure, since second actuator 70' is closed, the fluid pressure is sufficiently high to overcome the internal resilience of said first outlet fluid circuit valve 55'. Consequently, the second fluid is finally delivered (arrow B') by sequentially discharging it from first and second sub-chambers 35', 36' of second chamber 31'. In fact, since first and second outlet fluid circuit valves 55', 56' are one-way valves, the second fluid cannot flow back through the under-pressurized pathway and thus it is necessarily forced to be delivered (arrow B').

Operation of alternative delivery system 200' shown in FIG. 5 is disclosed in detail in the following with reference to FIG. 11 and FIG. 12, said operation being substantially identical to the method steps disclosed above with reference to fluid delivery system 100' of FIG. 2.

As a first initiation step, the method of delivery according to the present disclosure comprises the step of filling first and second sub-chambers 35, 36 of first pump module 30 with the first fluid and, analogously, the step of filling first and second sub-chambers 35', 36' of second pump module 30' with the second fluid. In order to perform said filling steps, processor P opens first and second supply station valves 11, 11', it closes first and second actuators 270, 270' of first and second recirculation fluid circuits 260, 260' and it acts on driving unit M for moving the common piston 32 within first and second chambers 31, 31', thereby allowing the first and the second fluids to exiting first and second supply stations 10, 10' respectively, and to flowing through first and second inlet fluid circuits 40, 40'. In detail, as soon as piston 32 is axially translated along a first direction (e.g. arrow C of FIG. 11), under-pressure is generated in the first sub-chambers (e.g. sub-chambers 35, 35') which are increasing their volume due to the piston axial movement. Therefore, the respective fluids are allowed to flow through first 41, 41' and second 42, 42' inlet fluid pathways of first and second inlet fluid circuits 40, 40', through the corresponding first inlet fluid circuit valves (e.g. first inlet fluid circuit valves 45, 45'), and then they enter and fill said first sub-chambers 35, 35'. At the same time, the air contained within the second sub-chambers (e.g. sub-chambers 36, 36')—which are decreasing their volume due to the piston axial movement (arrow C)—is primed away from the delivery system through venting means possessed by the opposite second inlet fluid circuit valves (e.g. second inlet fluid circuit valves 47, 47'). In fact, the air contained in said second sub-chambers 36, 36' is generally forced to exit said sub-chambers by passing through second inlet ports 46, 46', then through third inlet fluid pathways 43, 43' and finally through said second inlet fluid circuit valves 47, 47'. Successively, in order to fill the second sub-chambers with the respective fluids and to prime the first sub-chambers (i.e. expelling air therefrom), processor P acts on driving unit M for inverting the piston movement so that the piston is axially translated along a second direction opposite to the first direction (e.g. arrow D of FIG. 12). Since first and second actuators 270, 270' are kept closed while the piston is moving during the filling and priming steps, under-pressure is generated in the second sub-chambers (e.g. sub-chambers 36, 36') which are increasing their volume due to the piston axial movement (arrow D). Therefore, the first and second fluids are allowed to flow through first 41, 41' and third 43, 43' inlet fluid pathways of first and second inlet fluid circuits 40, 40' respectively, through the corresponding second inlet fluid circuit valves (e.g. second inlet fluid circuit valves 47, 47'), and then they enter and fill said second sub-chambers 36, 36'. At the same time, the air still contained within the first sub-chambers (e.g. sub-chambers 35, 35')—which are decreasing their volume due to the piston axial movement (arrow D)—is primed away from the delivery system through venting means possessed by the corresponding first inlet fluid circuit valves (e.g. first inlet fluid circuit valves 45, 45'). In fact, the air contained in said first sub-chambers 35, 35' is generally forced to exit said sub-chambers by passing through first inlet ports 44, 44', then through second inlet fluid pathways 42, 42' and finally through said first inlet fluid circuit valves 45, 45'. During the priming steps some amounts of the first fluid and of the second fluid exit from the delivery system through first and second outlet fluid circuits 50, 50' so that priming of also said first and second outlet fluid circuits 50, 50' can be performed.

Alternatively, air priming of the fluid delivery system is performed by dedicated venting means (not shown in the drawings) which is separate from the fluid circuit valves. According to an alternative embodiment, a dedicated venting means is associated with each valve of the fluid delivery system. According to a further alternative embodiment, a dedicated venting means is associated with each actuator 270, 270' of first and second recirculation fluid circuits 260, 260'.

As soon as chambers 31, 31' are filled up with the first fluid and the second fluid, respectively, and priming of the delivery system is completed, processor P closes first and second supply station valves 11, 11' and it opens first and second actuators 270, 270' of first and second recirculation fluid circuits 260, 260', while driving unit M is still operated, thereby keeping piston 32 axially translating (arrows C and D) within first and second chambers 31, 31'. Alternatively, processor P opens first and second actuators 270, 270' of first and second recirculation fluid circuits 260, 260' while first and second supply station valves 11, 11' are kept in their open working state when the two fluids are recirculated inside their respective chambers 31, 31'.

Figure 11:
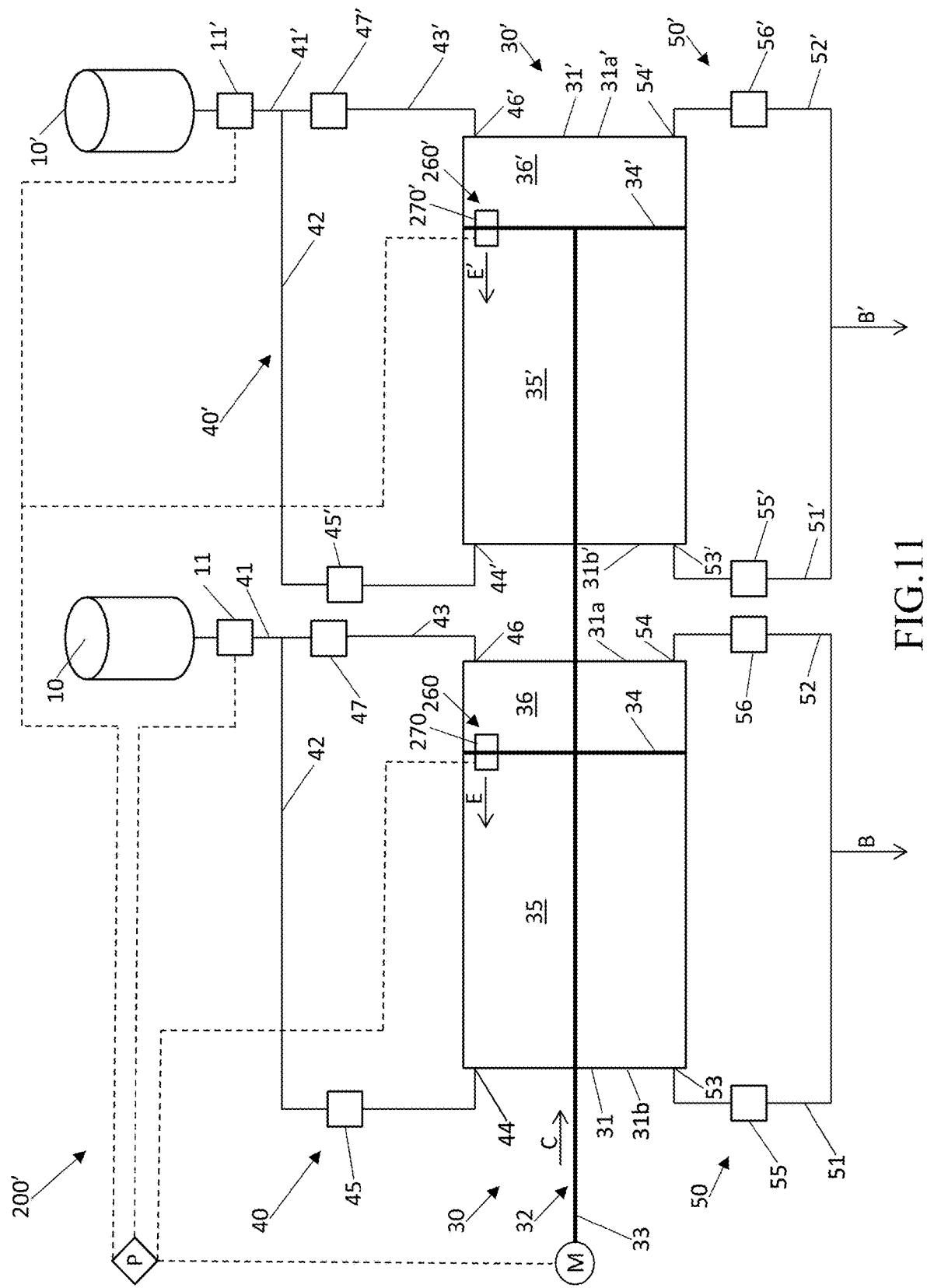
FIG. 11 to FIG. 12 show a schematic representation of the operation steps of the fluid delivery system shown in FIG. 5.

First actuator 270 is designed so that, when piston 32 is advanced in a first direction (see arrow C of FIG. 11), it allows the first fluid (flowing through first recirculation fluid circuit 260) to move in a second direction, opposite to first direction (see arrow E of FIG. 11). Therefore, translation of plunger 34 along said first direction causes a volume increase of first sub-chamber 35 and a corresponding volume decrease of second sub-chamber 36, meanwhile the first fluid initially contained within second sub-chamber 36 enters first sub-chamber 35 passing through first recirculation fluid circuit 260 and first actuator 270 associated thereto.

Analogously, second actuator 270' is designed so that, when piston 32 is advanced in a first direction (see arrow C of FIG. 11), it allows the second fluid (flowing through second recirculation fluid circuit 260') to move in a second direction, opposite to first direction (see arrow E' of FIG. 11). Therefore, translation of plunger 34' along said first direction causes a volume increase of first sub-chamber 35' and a corresponding volume decrease of second sub-chamber 36', meanwhile the second fluid initially contained within second sub-chamber 36' enters first sub-chamber 35' passing through second recirculation fluid circuit 260' and second actuator 270' associated thereto.

By keeping first and second actuators 270, 270' of first and second recirculation fluid circuits 260, 260' in their open working state, fluid delivery system 200' is prevented from delivering the first and the second fluids outside thereof. In fact, thanks to the open working state of first and second actuators 270, 270' and to the axial translation of piston 32, the first fluid is continuously recirculated within first chamber 31 through first recirculation fluid circuit 260, while the second fluid is continuously recirculated within second chamber 31' through second recirculation fluid circuit 260'. In detail, when piston 32 is moved in a first direction (e.g. arrow C of FIG. 11), the first fluid contained in second sub-chamber 36 is pushed through first recirculation fluid circuit 260 and through first actuator 270 to enter first sub-chamber 35. At the same time, the second fluid contained in second sub-chamber 36' is pushed through second recirculation fluid circuit 260' and through second actuator 270' to enter first sub-chamber 35'.

Figure 12:
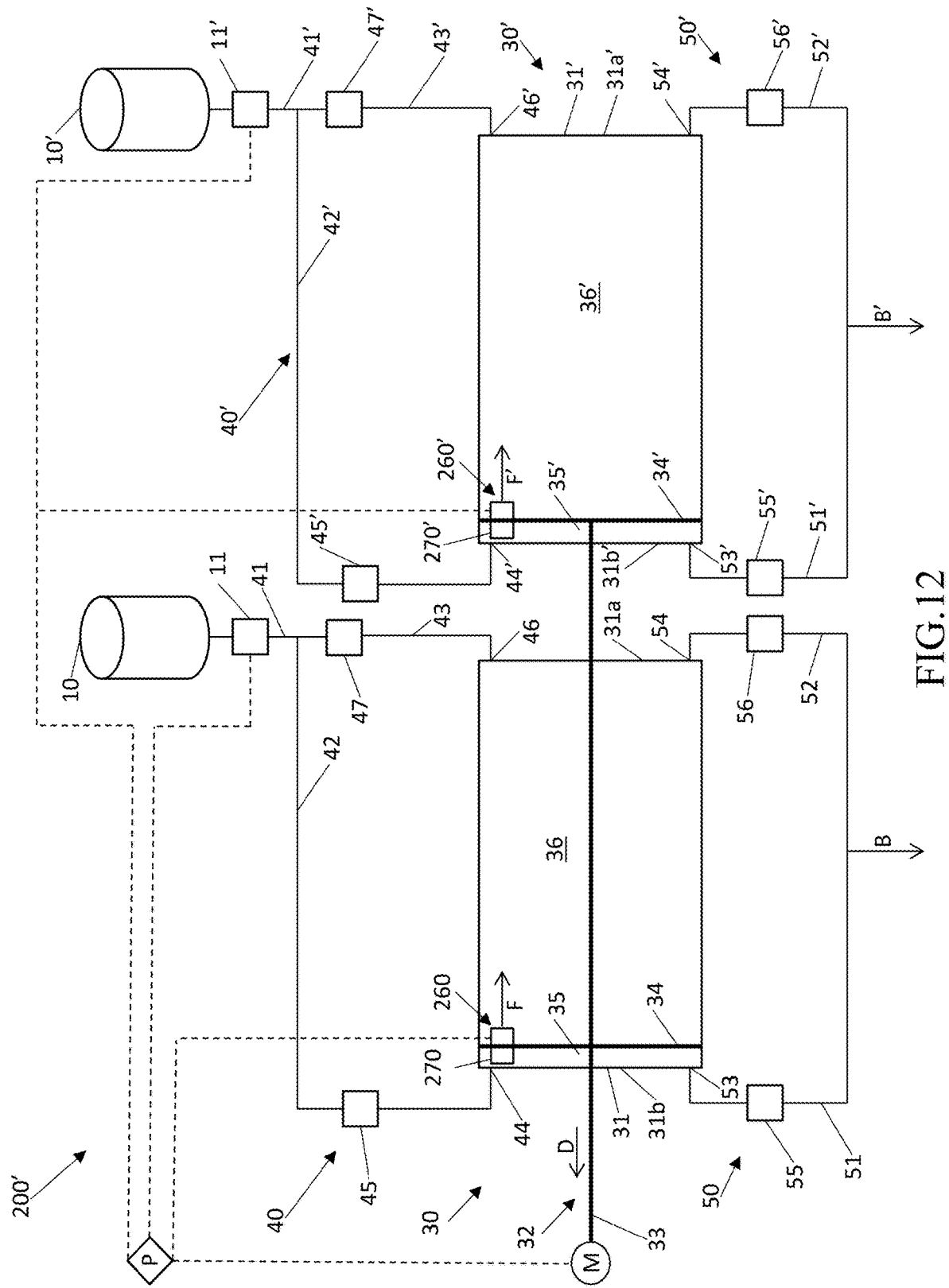

Thereafter, when piston 32 has reached its first end-stop, i.e. plunger 34 has completed its axial translation in said first direction (right direction of FIG. 11—see arrow C) and it has arrived in proximity of base wall 31a of first chamber 31 and, simultaneously, plunger 34' has arrived in proximity of base wall 31a' of second chamber 31', processor P acts on driving unit M to reverse piston axial translation (left direction of FIG. 12—see arrow D). Analogously to the piston first run described above, the first fluid contained in first sub-chamber 35 is pushed through first recirculation fluid circuit 260 and through first actuator 270 to enter second sub-chamber 36 (see arrow F of FIG. 12). At the same time, the second fluid contained in first sub-chamber 35' is pushed through second recirculation fluid circuit 260' and through second actuator 270' to enter second sub-chamber 36' (see arrow F' of FIG. 12).

Then, as soon as piston 32 has reached its second end-stop, i.e. plungers 34, 34' have completed their axial translations in the second direction (left direction in FIG. 12—see arrow D) and they arrive in proximity of base walls 31b, 31b' of respective first and second chambers 31, 31' (so that first sub-chambers 35, 35' contain a substantially small volume of respective fluids while second sub-chamber 36, 36' contain a large volume of respective fluids), processor P acts on driving unit M to reverse again piston axial translation (right direction in FIG. 11— see arrow C), thereby starting a new charge/discharge cycle of first and second chambers 31, 31' of fluid delivery system 200'. Of course, any number of cycles can be arranged for, said number depending on the requirements of the specific fluids to be delivered and on the specific application in which the delivery system is implemented. As already mentioned above, said initial recirculating steps of the two fluids within their respective chambers are particularly advantageous since they allow keeping the two fluids moving within the fluid delivery system, thereby ensuring proper and homogeneous shaking of each single fluid before delivery thereof.

As soon as recirculation is completed (e.g. the desired homogeneity of one fluid or of both fluids is successfully reached and, at a certain point in time, the delivery of the first fluid and/or of the second fluid is requested to be started), processor P suitably acts on first or second actuators 270, 270' to close it and to stop the recirculation step of at least one of said first and second fluids.

For example, in case only the first fluid contained within supply station 10 is requested to be delivered, processor P closes first actuator 270 of first recirculation fluid circuit 260, while second actuator 270' of second recirculation fluid circuit 260' is still kept in its open working condition so that delivery (arrow B) of the first fluid can be performed, while the second fluid is kept recirculating inside its respective second chamber 31'. This is the case, for instance, in which at a given time of an injection/infusion procedure performed on a given patient undergoing a medical examination (e.g. a CT diagnostic examination), delivery system 200' is requested to deliver only the first fluid (e.g. contrast agent) contained within supply station 10, while recirculation of the second fluid (e.g. saline solution) is performed (i.e. the second fluid is not delivered outside of the fluid delivery system at that specific moment in time).

Therefore, the method of delivery according to the present disclosure comprises the step of starting delivery (i.e. delivery outside of the fluid delivery system) of the first fluid contained within first chamber 31. In order to perform said step, as mentioned above processor P closes first actuator 270 of first recirculation fluid circuit 260 and it opens first supply station valve 11. During delivery of the first fluid (fluid exiting the delivery system—see arrow B), first supply station valve 11 is maintained in its open state because it is important to refill sub-chambers 35, 36 of first chamber 31 with new first fluid in order to avoid fluidic perturbations possibly impacting on the correct functioning of the piston and, consequently, of the overall delivery system. Since closing first actuator 270 prevents first fluid from flowing through first recirculation fluid circuit 260 (while, as already mentioned above, first and second inlet fluid circuit valves 45, 47 do not allow any flow back of the first fluid towards first supply station 10), pushing first plunger 34 in the first direction (arrow C of FIG. 11) and in the second opposite direction (arrow D of FIG. 12) allows the first fluid to exit, respectively, second outlet port 54 and first outlet port 53 of first chamber 31. Therefore, when the first fluid is pushed to pass through second outlet port 54 (arrow C), the first fluid flows into second outlet fluid pathway 52 of first outlet fluid circuit 50 and then it passes through second outlet fluid circuit valve 56 because at this stage of the procedure, since first actuator 270 is closed, the fluid pressure is sufficiently high to overcome the internal resilience of said second outlet fluid circuit valve 56. Analogously, when the first fluid is pushed to pass through first outlet port 53 (arrow D), the first fluid flows into first outlet fluid pathway 51 of first outlet fluid circuit 50 and then it passes through first outlet fluid circuit valve 55 because at this stage of the procedure, since first actuator 270 is closed, the fluid pressure is sufficiently high to overcome the internal resilience of said first outlet fluid circuit valve 55. Consequently, the first fluid is finally delivered (arrow B) by sequentially discharging it from first and second sub-chambers 35, 36 of first chamber 31. In fact, since first and second outlet fluid circuit valves 55, 56 are one-way valves, the first fluid cannot flow back through the under-pressurized pathway and thus it is forced to be delivered (arrow B).

Analogously, as soon as delivery of the first fluid (e.g. contrast agent) contained within first supply station 10 is requested to be terminated and delivery of the second fluid (e.g. saline solution) contained within second supply station 10' is requested to be started, processor P opens first actuator 270 of first recirculation fluid circuit 260 and it closes second actuator 270' of second recirculation fluid circuit 260' so that delivery (arrow B') of the second fluid is performed while the first fluid is recirculated inside its respective first chamber 31.

Therefore, the method of delivery according to the present disclosure further comprises the step of starting delivery (i.e. delivery outside of the fluid delivery system) of the second fluid contained within first chamber 31'. In order to perform said step, as mentioned above processor P closes first actuator 270' of second recirculation fluid circuit 260' and it opens second supply station valve 11'. During delivery of the second fluid (fluid exiting the delivery system—see arrow B'), second supply station valve 11' is maintained in its open state because it is important to refill sub-chambers 35', 36' of second chamber 31' with new second fluid in order to avoid fluidic perturbations possibly impacting on the correct functioning of the piston and, consequently, of the overall delivery system. Since closing second actuator 270' prevents second fluid from flowing through second recirculation fluid circuit 260' (while, as already mentioned above, first and second inlet fluid circuit valves 45', 47' do not allow any flow back of the second fluid towards second supply station 10'), pushing second plunger 34' in the first direction (arrow C of FIG. 11) and in the second opposite direction (arrow D of FIG. 12) allows the second fluid to exit, respectively, second outlet port 54' and first outlet port 53' of second chamber 31'. Therefore, when the second fluid is pushed to pass through second outlet port 54' (arrow C), the second fluid flows into second outlet fluid pathway 52' of second outlet fluid circuit 50' and then it passes through second outlet fluid circuit valve 56' because at this stage of the procedure, since second actuator 270' is closed, the fluid pressure is sufficiently high to overcome the internal resilience of said second outlet fluid circuit valve 56'. Analogously, when the second fluid is pushed to pass through first outlet port 53' (arrow D), the second fluid flows into first outlet fluid pathway 51' of second outlet fluid circuit 50' and then it passes through first outlet fluid circuit valve 55' because at this stage of the procedure, since second actuator 270' is closed, the fluid pressure is sufficiently high to overcome the internal resilience of said first outlet fluid circuit valve 55'. Consequently, the second fluid is finally delivered (arrow B') by sequentially discharging it from first and second sub-chambers 35', 36' of second chamber 31'. In fact, since first and second outlet fluid circuit valves 55', 56' are one-way valves, the second fluid cannot flow back through the under-pressurized pathway and thus it is forced to be delivered (arrow B').

According to the present disclosure, performing a step of mixing the two different fluids and successively a step of delivering the obtained mixture of said two fluids is described herein below with reference to the fluid delivery systems shown in FIG. 8 and FIG. 13.

Therefore, according to the embodiment of FIG. 8, a first fluid (e.g. a contrast agent, in case fluid delivery system 500 is applied to the medical field) is contained in first supply station 10, while a second fluid (e.g. a saline solution, in case fluid delivery system 500 is applied to the medical field) is contained in second supply station 10' as well as in additional first supply station 510, said first fluid being different from said second fluid.

Let's assume that fluid delivery system 500 is requested to deliver, for instance, a first given volume of the second fluid, followed by a second given volume of a mixture of the first fluid and the second fluid, and finally followed by a third given volume of the second fluid, thereby defining the delivery protocol (injection protocol) to be administered to a given patient.

As far as second chamber 31' is concerned, since only the second fluid is contained therein, the priming and filling steps of said second chamber 31' are performed analogously to the respective steps previously disclosed with reference to the embodiments of FIG. 9 and FIG. 10.

With reference to first chamber 31, the filling step is performed by allowing an amount of first fluid to enter second sub-chamber 36 and an amount of second fluid to enter first sub-chamber 35. This is achieved by opening first supply station valve 11 and additional supply station valve 511, while initially keeping first actuator 70 in its closed working condition. Therefore, thanks to the back and forth translational movement of piston 32 (which is common to both first and second chambers 31, 31'), under pressure is alternatively generated in the two first and second sub-chambers 35, 36, thereby allowing the respective fluids to enter the respective sub-chambers, and also allowing priming of first inlet fluid circuit 40, of first and second sub-chambers 35, 36 and of first outlet fluid circuit 50, as already disclosed above in the present description. As soon as the desired amounts of first and second fluids have entered first chamber 31, processor P closes first supply station valve 11 and additional supply station valve 511, and it opens first actuator 70. Therefore, recirculation of the first fluid from the second sub-chamber 36 into the first sub-chamber 35 as well as recirculation of the second fluid from the first sub-chamber 35 into the second sub-chamber 36 (due to inversion movement of piston 32) are allowed to occur, thereby mixing the first fluid with the second fluid to finally obtain the desired mixture to be delivered.

As already mentioned above, it can be pointed out that, according to this embodiment, a contrast agent at high concentration (e.g. ISOVUE®-370) can be used as first fluid while a saline solution is used as second fluid, so that, by suitably mixing the high concentrated contrast agent with the saline solution, the fluid delivery system would be able to provide volumes of contrast agent at different concentrations by starting from one single type of high concentrated contrast agent. This represents a very advantageous feature of the present disclosure since processor P can be programmed to calculate the volumes of the first and second fluids that are needed to be mixed for obtaining a mixture at a desired concentration which best fits with the specific patient to be treated (taking into account, for instance, his age, weight, gender, race, clinical conditions, . . . ) as well as with the specific examination to be performed (scan examination typology, body district to be examined, . . . ).

In accordance with the exemplified delivery protocol mentioned above, as soon as filling and priming steps are completed, the step of delivering the second fluid (e.g. saline solution in the given example) is performed by closing second actuator 70', thereby interrupting recirculation of said second fluid within second chamber 31'. Simultaneously to the step of delivering the second fluid, the step of mixing the first fluid and the second fluid within first chamber 31 is performed as indicated above by opening first actuator 70 of first recirculation fluid circuit 60. As soon as the requested first volume of the second fluid has been delivered (arrow B') outside of fluid delivery system 500, second actuator 70' of second recirculation fluid circuit 60' is activated by processor P to reach its open working state, so that recirculation of the second fluid within second chamber 31' is allowed and delivery of the second fluid outside of delivery system 500 is interrupted. Meanwhile, processor P closes first actuator 70 in order to stop recirculation of the mixed first fluid and second fluid within first chamber 31, thereby allowing the resulting mixture (at the desired contrast agent concentration) to be delivered (arrow B) outside of fluid delivery system 500. Thereafter, as soon as the requested second volume of the desired mixture is delivered, processor P opens first actuator 70 for allowing recirculation of the mixed first fluid and second fluid within first chamber 31, and processor P also closes second actuator 70' so that a final third volume of the second fluid can be delivered in accordance with the exemplified delivery protocol mentioned above.

Figure 13:
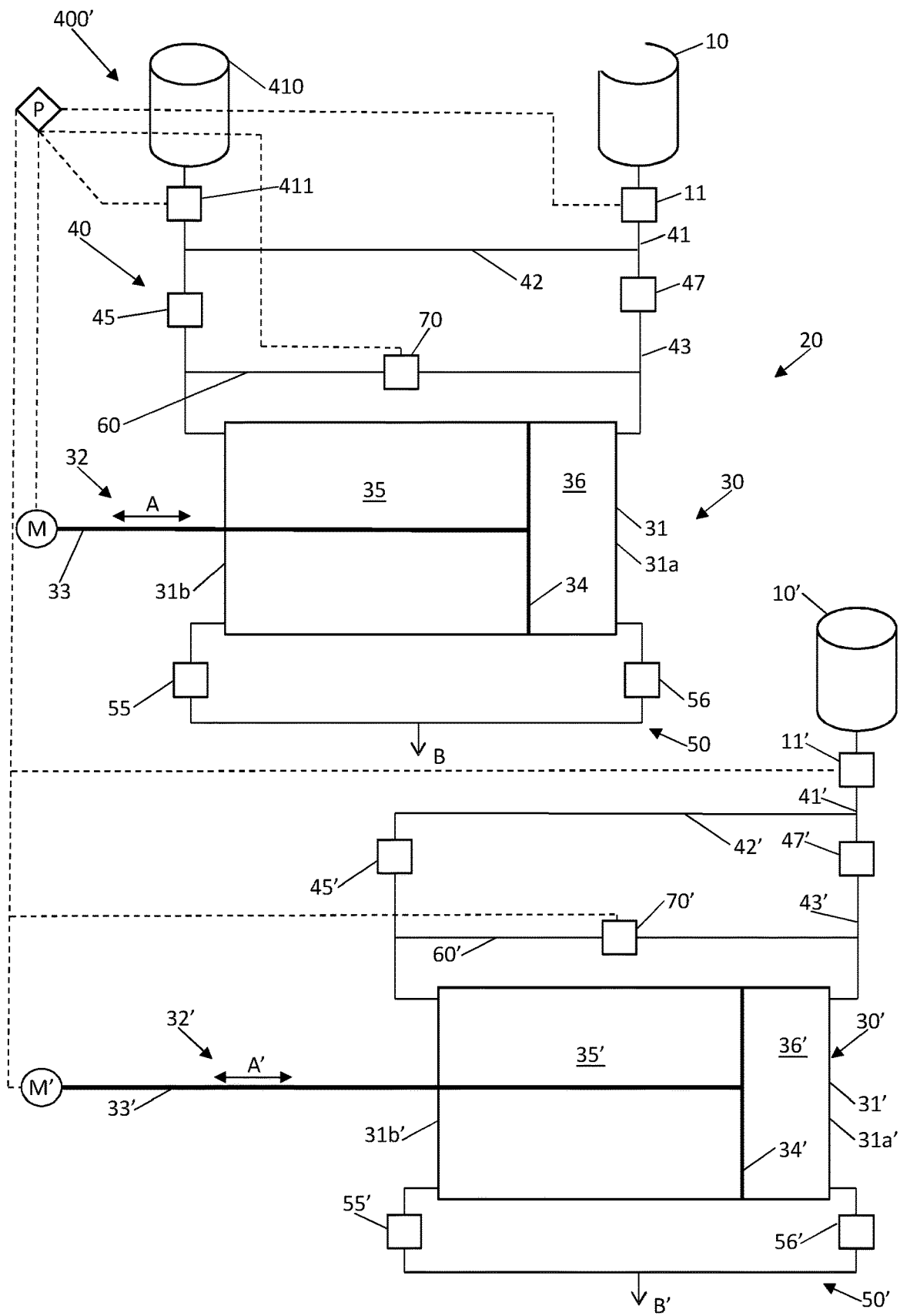
FIG. 13 shows a schematic representation of an alternative solution of the embodiment of FIG. 7.

According to the alternative embodiment of FIG. 13, a first fluid (e.g. a contrast agent, in case fluid delivery system 400' is applied to the medical field) is contained in first supply station 10, while a second fluid (e.g. a saline solution, in case fluid delivery system 400' is applied to the medical field) is contained in second supply station 10' as well as in additional first supply station 410, said first fluid being different from said second fluid.

As indicated above with reference to the embodiment of FIG. 8, let's assume that fluid delivery system 400' is requested to deliver, for instance, a first volume of the second fluid, followed by a second volume of a mixture of the first fluid and the second fluid, and finally followed by a third volume of the second fluid.

As far as second chamber 31' is concerned, since only the second fluid is contained therein, the priming and filling steps of said second chamber 31' are performed analogously to the respective steps previously disclosed with reference to the embodiments of FIG. 9 and FIG. 10.

With reference to first chamber 31, the filling step is performed by allowing a given amount of first fluid to enter second sub-chamber 36 and a given amount of second fluid to enter first sub-chamber 35. This is achieved by opening first supply station valve 11 and additional supply station valve 411, while initially keeping first actuator 70 in its closed working condition. Therefore, thanks to the back and forth translational movement of piston 32, under pressure is alternatively generated in the first and second sub-chambers 35, 36, thereby allowing the respective fluids to enter the respective sub-chambers, and also allowing priming of first inlet fluid circuit 40, first and second sub-chambers 35, 36 and first outlet fluid circuit 50. As soon as the desired amounts of first and second fluids have entered first chamber 31, processor P closes first supply station valve 11 and additional supply station valve 511, and it opens first actuator 70. Therefore, recirculation of the first fluid from the second sub-chamber 36 into the first sub-chamber 35 as well as recirculation of the second fluid from the first sub-chamber 35 into the second sub-chamber 36 (due to inversion movement of piston 32) are allowed to occur, thereby mixing the first fluid and the second fluid to finally obtain the desired mixture to be delivered.

In accordance with the exemplified delivery protocol mentioned above, as soon as filling and priming steps are completed, the step of delivery of the second fluid (saline solution in the given example) is performed by closing second actuator 70', thereby interrupting recirculation of said second fluid within second chamber 31'. Preferably, simultaneously to the step of delivering the second fluid, the step of mixing the first fluid and the second fluid within first chamber 31 is performed as indicated above by opening first actuator 70 of first recirculation fluid circuit 60. As soon as the requested first volume of the second fluid has been delivered (arrow B') outside of fluid delivery system 400', second actuator 70' of second recirculation fluid circuit 60' is activated by processor P to reach its open working state, so that recirculation of the second fluid within second chamber 31' is allowed and delivery of the second fluid outside of delivery system 400' is interrupted. Meanwhile, processor P closes first actuator 70 in order to stop recirculation of the mixed first fluid and second fluid within first chamber 31, thereby allowing the resulting mixture (at the desired contrast agent concentration) to be delivered (arrow B) outside of fluid delivery system 400'. Thereafter, as soon as the requested second volume of the desired mixture is delivered, processor P opens first actuator 70 for allowing recirculation of the mixed first fluid and second fluid within first chamber 31 and processor P also closes second actuator 70' so that a final third volume of the second fluid can be delivered in accordance with the exemplified delivery protocol mentioned above.

Figure 7:
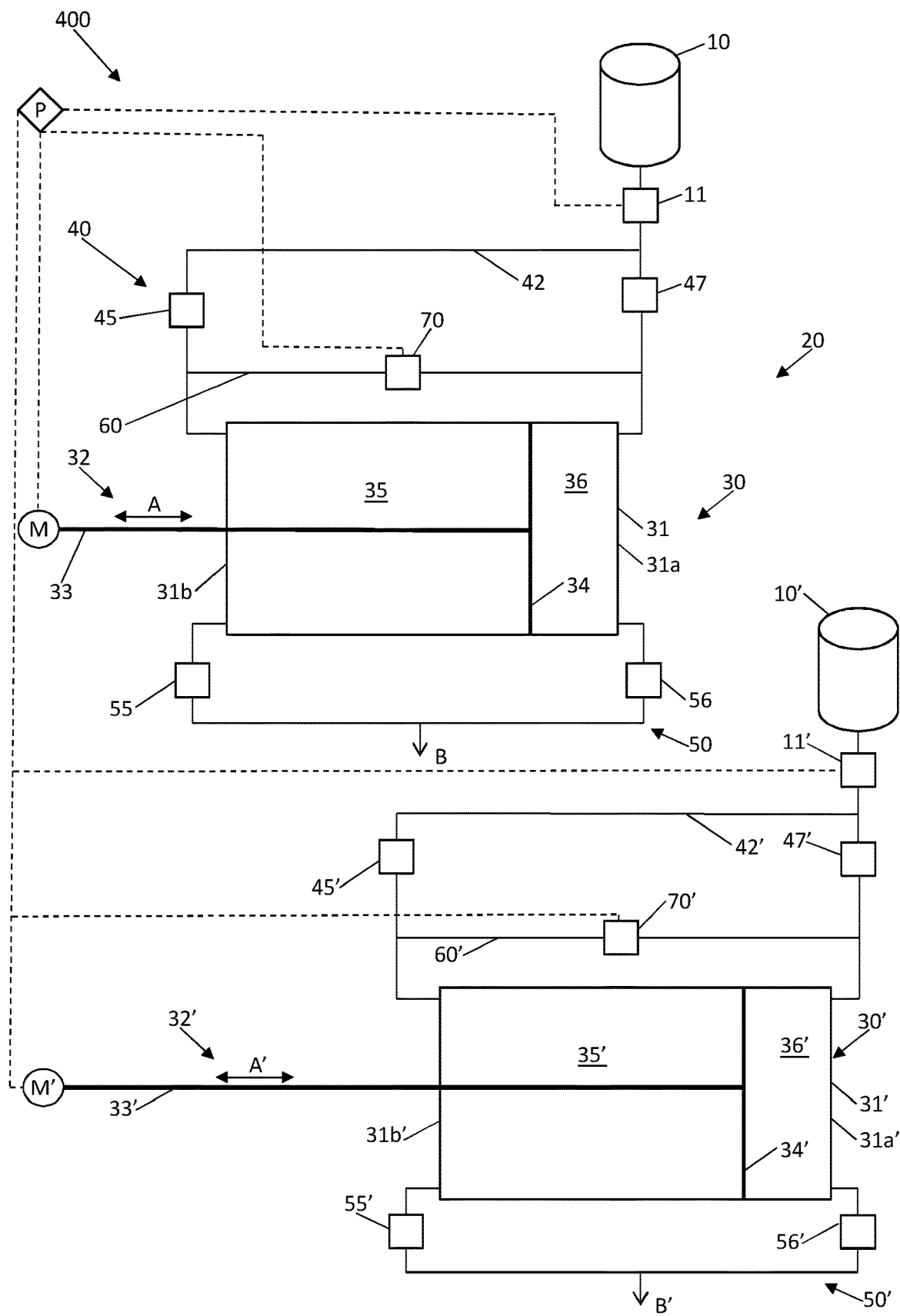
FIG. 7 shows a schematic representation of an alternative solution of the embodiment of FIG. 1.
Figure 14:
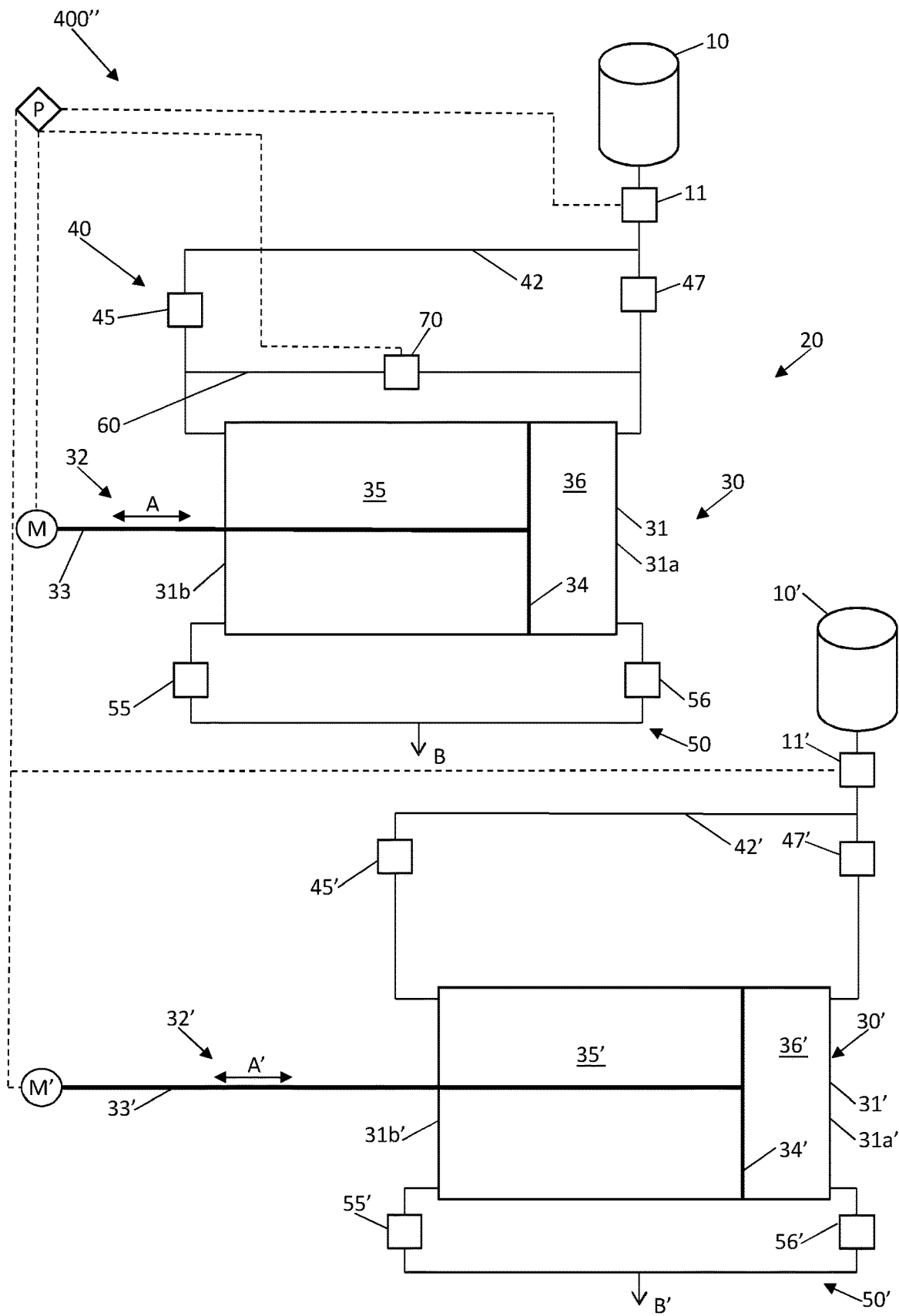
FIG. 14 shows a schematic representation of a further alternative solution of the embodiment of FIG. 7.

According to a further embodiment shown in FIG. 14, fluid delivery system 400" is very similar to fluid delivery system 400 of FIG. 7 with the difference that a second recirculation fluid circuit is not envisaged. In fact, in case the second fluid contained within second supply station 10' is not requested to be recirculated within second chamber 31' because, for instance, there's no need to keep or reach a given homogeneity of said second fluid (e.g. in case the second fluid is a saline solution), thanks to the fact that fluid delivery system 400" comprises two separate and independent driving units M, M', delivery of the second fluid (arrow B') is performed by processor P through activation of driving unit M' (and thus through the movement of second piston 32') exactly at the given moment in which the second fluid is requested to be delivered. In other words, according to this embodiment second chamber 31' of second pump module 30' can be filled in and discharged without any need of recirculating the second fluid within said second chamber 31'.

Modifications

In order to satisfy local and specific requirements, a person skilled in the art may apply many logical and/or physical modifications and alterations to the present disclosure. More specifically, although this disclosure has been described with a certain degree of particularity with reference to one or more embodiments thereof, it should be understood that various omissions, substitutions and changes in the form and details as well as other embodiments are possible. Particularly, different embodiments of the present disclosure may even be practiced without the specific details (such as the numerical values) set forth in the preceding description to provide a more thorough understanding thereof. Conversely, well-known features may have been omitted or simplified in order not to obscure the description with unnecessary details. Moreover, it is expressly intended that specific elements and/or method steps described in connection with any embodiment of the present disclosure may be incorporated in any other embodiment as a matter of general design choice. In any case, each numerical value should be read as modified by the term about (unless already done) and each range of numerical values should be intended as expressly specifying any possible number along the continuum within the range (comprising its end points). Moreover, ordinal or other qualifiers are merely used as labels to distinguish elements with the same name but do not by themselves connote any priority, precedence or order. The terms include, comprise, have, contain and involve (and any forms thereof) should be intended with an open, non-exhaustive meaning (i.e., not limited to the recited items); the terms based on, dependent on, according to, function of (and any forms thereof) should be intended as a non-exclusive relationship (i.e., with possible further variables involved); the term a/an should be intended as one or more items (unless expressly indicated otherwise); the term means for (or any means-plus-function formulation) should be intended as any structure adapted or configured for carrying out the relevant function.

As disclosed above, the actuators of the recirculation fluid circuits and the supply station valves are active components controlled by processor P, while the remaining valves of the fluid delivery system are check valves which do not require to be acted by processor P. According to a further embodiment (not shown in the figures), in order to enhance safety and reliability of the fluid delivery system of the present disclosure, all the valves of the fluid delivery system are active mechanical valves or active mechanical clamps that are controlled by processor P. In detail, said active mechanical valves/clamps are mechanical gates that open/close the fluid pathway by radially acting on the external surface thereof.

According to an embodiment of the present invention (not shown in the figures), the volume of the supply stations is remarkably greater than the volume of the chambers of the fluid delivery system. This aspect is particularly advantageous since it ensures that a high number of deliveries (e.g. of injections or infusions) can be performed without requesting frequent changes of the fluids containers and, moreover, it ensures that the overall size of the fluid delivery system can be advantageously minimized, thereby making it more flexible, less cumbersome, portable (if needed) and also less expensive.

According to a further embodiment, the method of operating the fluid delivery system of the present disclosure comprises the step of computing the amount (volume) of fluids to be delivered for a given application and, successively, the step of axially translating the piston(s) to define sub-chambers whose volumes are substantially equal to the computed fluid volumes to be delivered. This aspect is of particular interest when a low amount of fluid is requested to be delivered (i.e. lower than the chamber volume of the fluid delivery system) and thus it would be preferable to deliver such low amount while the piston is axially translating along one direction only, thereby avoiding reversal of the piston movement and also avoiding possible delivery perturbations/delays related thereto.

Alternatively, the step of computing is not performed by the control unit of the fluid delivery system. On the contrary, the volume to be delivered is computed off-line and successively provided to the processor as a delivery input data. Therefore, immediately before the step of delivering is started, the piston(s) is/are axially translated to define sub-chambers having volumes corresponding to said computed volume.

According to an alternative application (not shown in the figures), the delivery system of the present disclosure can be used not necessarily to deliver the at least first and second fluids, or more than two fluids, or a mixture thereof. Indeed, said delivery system can be used for dosing said fluids, thereby producing a customized preparation according to any specific need. For instance, in case the delivery system of the present disclosure is used in the medical field, two or more liquid medicines can be suitably dosed and successively collected into a suitable reservoir (e.g. a pouch) that is advantageously customized for a given patient, thereby reducing or even avoiding wastes of valuable and expensive substances. As mentioned above, the supply stations as well as the chambers (and thus the respective sub-chambers) of each pump module can have different and appropriate volumes so that delivery/administration/collection of the different fluids can be regulated (by suitably programming processor P) according to the real needs of each specific case. Customizing an injection, or customizing a given preparation to be successively administered (e.g. filling up a pouch for a subsequent intravenous administration), or even customizing the concentration of a given contrast agent to be injected are all advantageous aspects which render the delivery system of the present disclosure extremely versatile and valuable.

The delivery system of the present disclosure further allows to alternately deliver (or better to inject) very small and separate volumes of a first fluid and of a second fluid by quickly switching between the two pump modules (e.g. by having processor P to sequentially activate/de-activate the first and the second actuators of the first and the second recirculation fluid circuits). In other words, thanks to the delivery system of the present disclosure, the contrast agent and the saline solution can be administered (i.e. injected) to a patient in rapid alternate succession so that mixing of the contrast agent and the saline solution is achieved within an organ of the patient, for example within the heart. This particular injection phase (which is known as Diluject® or Rapid Phasing and it is a specific technical feature of CT Exprès® automatic syringe-less injector manufactured by Bracco Injeneering SA) can be performed with improved efficiency and reliability by using the delivery system of the present disclosure.

The following are preferred aspects and embodiments of the present disclosure.

1. A fluid delivery system (100; 100'; 100"; 200; 200'; 300; 400; 400'; 400"; 500) comprising:
    at least one first supply station (10) for supplying a first fluid and at least one second supply station (10') for supplying a second fluid, said second fluid being different from said first fluid;
    a pressurizing unit (20) for pressurizing the first fluid and the second fluid comprising:
        a first pump module (30) comprising a first chamber (31) and a first piston (32) contained therein, said first piston having a first plunger (34) that, in cooperation with internal walls of said first chamber (31), defines first (35) and second (36) variable-volume sub-chambers of said first chamber (31), and
        a second pump module (30') comprising a second chamber (31') and a second piston (32') contained therein, said second piston having a second plunger (34') that, in cooperation with internal walls of said second chamber (31'), defines first (35') and second (36') variable-volume sub-chambers of said second chamber (31');
    a first inlet fluid circuit (40) in fluid communication with said at least one first supply station (10) and with said first pump module (30) for supplying said first fluid to said first (35) and second (36) variable-volume sub-chambers of said first chamber (31);
    a second inlet fluid circuit (40') in fluid communication with said at least one second supply station (10') and with said second pump module (30') for supplying said second fluid to said first (35') and second (36') variable-volume sub-chambers of said second chamber (31');
    a first recirculation fluid circuit (60; 260) fluidically connecting said first (35) and second (36) variable-volume sub-chambers of said first chamber (31), and
    a first actuator (70; 270) for managing a fluid passage in both directions between said first (35) and second (36) variable-volume sub-chambers of said first chamber (31), said first actuator (70; 270) being part of said first recirculation fluid circuit (60).

2. The fluid delivery system (100; 100'; 100"; 200; 200'; 300; 400; 400'; 500) according to Embodiment 1, characterized in that it further comprises a second recirculation fluid circuit (60'; 260') fluidically connecting said first (35') and second (36') variable-volume sub-chambers of said second chamber (31').

3. The fluid delivery system (100; 100'; 100"; 200; 200'; 300; 400; 400'; 500) according to Embodiment 2, characterized in that it further comprises a second actuator (70'; 270') for managing the fluid passage in both directions between said first (35') and second (36') variable-volume sub-chambers of said second chamber (31'), said second actuator (70'; 270') being part of said second recirculation fluid circuit (60'; 260').

4. The fluid delivery system (100; 100'; 100"; 200; 200'; 300; 400; 400'; 400" 500) according to any of the preceding Embodiments, characterized in that the pressurizing unit (20) further comprises at least one driving unit (M; M') for reciprocating (A; A'; C; D) said first (32) and second (32') pistons within said first (31) and second (31') chambers respectively.

5. The fluid delivery system (100; 100'; 100"; 200; 200'; 300; 400; 400'; 400"; 500) according to any of the preceding Embodiments, characterized in that it further comprises a first outlet fluid circuit (50) in fluid communication with said first pump module (30) for discharging said first fluid alternatively from said first (35) and second (36) variable-volume sub-chambers of said first chamber (31), said first outlet fluid circuit (50) being separate from said first inlet fluid circuit (40).

6. The fluid delivery system (100; 100'; 100"; 200; 200'; 300; 400; 400'; 400"; 500) according to any of the preceding Embodiments, characterized in that it further comprises a second outlet fluid circuit (50') in fluid communication with said second pump module (30') for discharging said second fluid alternatively from said first (35') and second (36') variable-volume sub-chambers of said second chamber (31'), said second outlet fluid circuit (50') being separate from said second inlet fluid circuit (40').

7. The fluid delivery system (100; 200; 400; 400'; 400") according to any of the preceding Embodiments, characterized in that the first pump module (30) and the second pump module (30') are arranged in parallel.

8. The fluid delivery system (100; 200) according to Embodiment 7, characterized in that the first piston (32) and the second piston (32') are separate and are associated to a common single driving unit (M).

9. The fluid delivery system (400; 400'; 400") according to Embodiment 7, characterized in that the first piston (32) and the second piston (32') are separate and are associated to respective first (M) and second (M') driving units.

10. The fluid delivery system (100'; 100"; 200'; 300; 500) according to any of preceding Embodiments 1 to 6, characterized in that the first pump module (30) and the second pump module (30') are arranged in series.

11. The fluid delivery system (100'; 100"; 200'; 300; 500) according to Embodiment 10, characterized in that the first piston (32) and the second piston (32') define a common piston axially translating (A; A'; C; D) within said first (31) and second (31') chambers.

12. The fluid delivery system (100'; 100"; 200'; 300; 500) according to Embodiment 11, characterized in that said first (34) and second (34') plungers are spaced apart along said common piston (32), each plunger reciprocating within a corresponding chamber (31; 31').

13. The fluid delivery system (100; 100'; 100"; 200; 200'; 300; 400; 400'; 400"; 500) according to any of the preceding Embodiments, characterized in that the first (40) and second (40') inlet fluid circuits comprise a first inlet fluid pathway (41; 41') which is in fluid communication with said at least one first (10) and said at least one second (10') supply stations, said first inlet fluid pathway (41; 41') comprising a supply station valve (11; 11').

14. The fluid delivery system (100; 100'; 100"; 200; 200'; 300; 400; 400'; 400"; 500) according to Embodiment 13, characterized in that, downstream from said supply station valve (11; 11'), said first (40) and second (40') inlet fluid circuits comprise a second inlet fluid pathway (42; 42') and a third inlet fluid pathway (43; 43') which are in fluid communication respectively with said first variable-volume sub-chambers (35; 35') and with said second variable-volume sub-chambers (36; 36'), said second inlet fluid pathway (42; 42') being provided with a first inlet fluid circuit valve (45; 45'), and said third inlet fluid pathway (43) being provided with a second inlet fluid circuit valve (47; 47').

15. The fluid delivery system (100; 100'; 100"; 200; 200'; 300; 400; 400'; 400"; 500) according to Embodiments 5 and 6, characterized in that said first (50) and second (50') outlet fluid circuits comprise a first outlet fluid pathway (51; 51') and a second outlet fluid pathway (52; 52') which are in fluid communication respectively with said first variable-volume sub-chambers (35; 35') and with said second variable-volume sub-chambers (36; 36'), said first outlet fluid pathway (51; 51') being provided with a first outlet fluid circuit valve (55; 55') and said second outlet fluid pathway (52; 52') being provided with a second outlet fluid circuit valve (56; 56').

16. The fluid delivery system (100; 100'; 100"; 300; 400; 400'; 500) according to Embodiments 2 and 3, characterized in that said first (60) and second (60') recirculation fluid circuits and said first (70) and second (70') actuators associated thereto are external to said first (31) and second (31') chambers respectively.

17. The fluid delivery system (100; 100'; 100"; 300; 400; 400'; 500) according to Embodiment 16, characterized in that said first (60) and second (60') recirculation fluid circuits fluidically connect respectively with said second inlet fluid pathway (42; 42') downstream from said first inlet fluid circuit valve (45; 45') and with said third inlet fluid pathway (43; 43') downstream from said second inlet fluid circuit valve (47; 47').

18. The fluid delivery system (200; 200') according to Embodiments 2 and 3, characterized in that said first (260) and second (260') recirculation fluid circuits and said first (270) and second (270') actuators are respectively contained within said first (31) and second (31') chambers and are integral with said first (34) and second (34') plungers of the respective first (32) and second (32') pistons.

19. The fluid delivery system (200; 200') according to Embodiment 18, characterized in that said first (260) and second (260') recirculation fluid circuits respectively comprise a fluid passage obtained within the thickness of said first (34) and second (34') plungers for ensuring fluid communication between said first (35; 35') and second (36; 36') variable-volume sub-chambers.

20. The fluid delivery system (100; 100'; 100"; 200; 200'; 300; 400; 400'; 400"; 500) according to Embodiment 1, characterized in that it further comprises a processor (P) which controls and actuates said first actuator (70; 270).

21. The fluid delivery system (100; 100'; 100"; 200; 200'; 300; 400; 400'; 500) according to Embodiment 3, characterized in that it further comprises a processor (P) which controls and actuates said second actuator (70'; 270').

22. The fluid delivery system (100; 100'; 100"; 200; 200'; 300; 400; 400'; 400"; 500) according to Embodiment 13, characterized in that it further comprises a processor (P) which controls and actuates said supply station valve (11; 11').

23. The fluid delivery system (100; 100'; 100"; 200; 200'; 300; 400; 400'; 400"; 500) according to Embodiment 4, characterized in that it further comprises a processor (P) which controls and operates said at least one driving unit (M; M').

24. The fluid delivery system (400'; 500) according to any of the preceding Embodiments, characterized in that it further comprises an additional supply station (410; 510).

25. The fluid delivery system (100; 100'; 100"; 200; 200'; 300; 400; 400'; 400"; 500) according to Embodiments 20 to 22, characterized in that the first (70; 270) and second (70'; 270') actuators and the supply station valve (11; 11') are active valves actuated by said processor (P).

26. The fluid delivery system (100; 100'; 100"; 200; 200'; 300; 400; 400'; 400"; 500) according to Embodiment 20, characterized in that all the valves (70; 70'; 270; 270'; 11; 11'; 45; 45'; 47; 47'; 55; 55'; 56; 56') of the fluid delivery system are active mechanical clamps that are actuated by said control unit (P).

27. The fluid delivery system (100; 100'; 100"; 200; 200'; 300; 400; 400'; 400"; 500) according to any of the preceding Embodiments, characterized in that the volume of the first (10) and second (10') supply stations is remarkably greater than the volume of the first (31) and second (31') chambers of the fluid delivery system.

28. The fluid delivery system (100; 100'; 100"; 200; 200'; 300; 400; 400'; 400"; 500) according to any of the preceding Embodiments, characterized in that said fluid delivery system is an injection system, and said first and second fluids are medical fluids selected from a liquid medicament, a drug, a diagnostically active contrast agent, a saline solution or a mixture thereof 29. A method of operating a fluid delivery system (100; 100'; 100"; 200; 200'; 300; 400; 400'; 400"; 500) for delivering at least a first fluid and a second fluid, said first fluid being different from said second fluid, said method comprising:
    a step of delivering the second fluid outside of the fluid delivery system;
    a step of recirculating the first fluid internally to the fluid delivery system, and
    a step of delivering the first fluid outside of the fluid delivery system.

30. The method of operating according to Embodiment 29, characterized in that the step of delivering the second fluid outside of the fluid delivery system is performed simultaneously to the step of recirculating the first fluid internally to the fluid delivery system.

31. The method of operating according to Embodiments 29 and 30, characterized in that the step of delivering the first fluid outside of the fluid delivery system is performed after the step of delivering the second fluid outside of the fluid delivery system has been stopped.

32. A method of operating a fluid delivery system (100; 100'; 100"; 200; 200'; 300; 400; 400'; 500) for delivering at least a first fluid and a second fluid, said first fluid being different from said second fluid, said method comprising:
- a step of delivering the first fluid outside of the fluid delivery system;
- a step of recirculating the second fluid internally to the fluid delivery system;
- a step of delivering the second fluid outside of the fluid delivery system, and
- a step of recirculating the first fluid internally to the fluid delivery system.

33. The method of operating according to Embodiment 32, characterized in that the step of recirculating the second fluid internally to the fluid delivery system is performed substantially simultaneously to the step of delivering the first fluid outside of the fluid delivery system.

34. The method of operating according to Embodiments 32 and 33, characterized in that the step of recirculating the first fluid internally to the fluid delivery system is performed substantially simultaneously to the step of delivering the second fluid outside of the fluid delivery system.

35. The method of operating according to any of Embodiments from 32 to 34, characterized in that the step of delivering the first fluid outside of the fluid delivery system is performed alternately to the step of delivering the second fluid outside of the fluid delivery system.

36. A method of operating a fluid delivery system (100; 100'; 100"; 200; 200'; 300; 400; 400'; 400"; 500) comprising at least one first supply station (10) for supplying a first fluid and at least one second supply station (10') for supplying a second fluid, said second fluid being different from said first fluid, said fluid delivery system (100; 100'; 100"; 200; 200'; 300; 400; 400'; 500) further comprising a pressurizing unit (20) provided with a first pump module (30) and a second pump module (30'), each first and second pump module respectively comprising a chamber (31; 31') and a piston (32; 32') reciprocating (A; A'; C; D) therein, said piston (32; 32') having a plunger (34; 34') which, in cooperation with inner walls of said chamber (31; 31'), defines first (35; 35') and second (36; 36') variable-volume sub-chambers, the fluid delivery system (100; 100'; 100"; 200; 200'; 300; 400; 400'; 500) further comprising a first (60; 260) recirculation fluid pathway and a first actuator (70; 270) associated thereto for fluidically connecting said first (35) and second (36) variable-volume sub-chambers of said first (31) chamber, said method comprising the steps of:
- supplying the first fluid from the first supply station (10) to said first (35) and second (36) variable-volume sub-chambers of said first chamber (31);
- supplying the second fluid from the second supply station (10') to said first (35') and second (36') variable-volume sub-chambers of said second chamber (31');
- axially translating (A; A'; C; D) the respective pistons (32; 32') within said first (31) and second (31') chambers, and
- operating the first actuator (70; 270) for recirculating the first fluid within the first chamber (31).

37. The method of operating according to Embodiment 31, wherein said method further comprises a step of delivering said first fluid outside of said delivery system and a step of delivering said second fluid outside of said delivery system, said delivering steps being performed alternately to each other.

38. The method of operating according to Embodiment 36, wherein said fluid delivery system (100; 100'; 100"; 200; 200'; 300; 400; 400'; 500) further comprises a second (60'; 260') recirculation fluid pathway and a second actuator (70'; 270') associated thereto for fluidically connecting said first (35') and second (36') variable-volume sub-chambers of said second (31') chamber, said method further comprising the step of operating the second actuator (70'; 270') for recirculating the second fluid within the second chamber (31').

39. The method of operating according to Embodiments 37 and 38, wherein the step of delivering the first fluid outside of said delivery system is performed simultaneously with the step of recirculating the second fluid.

40. The method of operating according to Embodiments 37 and 38, wherein the step of delivering the second fluid outside of said delivery system is performed simultaneously with the step of recirculating the first fluid.

41. The method of operating according to any of Embodiments from 38 to 40, wherein the step of recirculating is performed by making the first fluid and the second fluid to flow respectively through said first (60; 260) and second (60'; 260') recirculation fluid pathways during multiple axial translations (A; A'; C; D) of the respective pistons (32; 32') within said first (31) and second (31') chambers.

42. The method of operating according to Embodiment 37, wherein the step of recirculating the first fluid is sequentially repeated till the step of delivering the second fluid out of the fluid delivery system is completed.

43. The method of operating according to Embodiment 38, wherein the step of recirculating the second fluid is sequentially repeated till the step of delivering the first fluid out of the fluid delivery system is completed.

44. The method of operating according to Embodiment 36, wherein said fluid delivery system (100; 100'; 100"; 200; 200'; 300; 400; 400'; 400"; 500) further comprises a valve (11) associated to said first supply station (10) and said pressurizing unit (20) further comprises at least one driving unit (M; M'), wherein the step of supplying the first fluid comprises the step of filling said first chamber (31) with said first fluid, the step of filling said first chamber (31) further comprising the steps of:
- opening said valve (11) associated to said first supply station (10);
- closing the first actuator (70; 270) of the first recirculation fluid pathway (60; 260), and
- acting on said driving unit (M) for reciprocating the piston (32) within said first chamber (31).

45. The method of operating according to Embodiment 38, wherein said fluid delivery system (100; 100'; 100"; 200; 200'; 300; 400; 400'; 500) further comprises a valve (11') associated to said second supply station (10') and said pressurizing unit (20) further comprises at least one driving unit (M; M'), wherein the step of supplying the second fluid comprises the step of filling said second chamber (31') with said second fluid, the step of filling said second chamber (31') further comprising the steps of:
- opening said valve (11') associated to said second supply station (10');

closing the second actuator (70'; 270') of the second recirculation fluid pathway (60'; 260'), and acting on said driving unit (M; M') for reciprocating the piston (32') within said second chamber (31').

46. The method of operating according to Embodiments 44 and 45, further comprising the step of priming air outside of the fluid delivery system, said step of priming being performed simultaneously to the steps of filling said first (31) and second (31') chambers.

47. The method of operating according to any of Embodiments 36 to 46, further comprising the steps of:

computing a volume of the first fluid and a volume of the second fluid to be delivered for a given application, and axially translating (A, A'; C; D) the respective piston (32; 32') to define sub-chambers (35; 36; 35'; 36') volumes to be substantially equal to the computed first fluid and second fluid volumes to be delivered.

48. The method of operating according to Embodiment 31, further comprising the steps of:

providing a volume of first fluid and a volume of second fluid to be delivered for a given application as input delivery data, and axially translating the respective piston (32; 32') to define sub-chambers (35; 36; 35'; 36') volumes to be substantially equal to the computed first fluid and second fluid volumes to be delivered.

49. A method of operating a fluid delivery system (400'; 400''; 500) for delivering a first fluid and a mixture of said first fluid with a second fluid, said first fluid being different from said second fluid, said method comprising:

a step of delivering said first fluid outside of said fluid delivery system;

a step of recirculating internally to the fluid delivery system said first fluid and said second fluid for making a mixture thereof, and a step of delivering said mixture outside of the fluid delivery system.

50. The method of operating a fluid delivery system (400'; 500) according to Embodiment 49, characterized in that it further comprises a step of recirculating said first fluid internally to the fluid delivery system.

51. The method of operating a fluid delivery system according to Embodiment 49, characterized in that said step of recirculating internally to the fluid delivery system said first fluid and said second fluid is performed substantially simultaneously to said first step of delivering the first fluid outside of the fluid delivery system.

52. The method of operating a fluid delivery system according to Embodiment 50, characterized in that the step of recirculating the first fluid internally to the fluid delivery system is performed substantially simultaneously to the step of delivering the mixture outside of the fluid delivery system.

53. The method of operating a fluid delivery system according to Embodiment 49, characterized in that the step of delivering the first fluid outside of the fluid delivery system is performed alternately to the step of delivering the second fluid outside of said fluid delivery system.

The invention claimed is:

1. A fluid delivery system (100; 100'; 100''; 200; 200'; 300; 400; 400'; 400''; 500) comprising:

at least one first supply station (10) for supplying a first fluid and at least one second supply station (10') for supplying a second fluid, said second fluid being different from said first fluid;

a pressurizing unit (20) for pressurizing the first fluid and the second fluid comprising:

a first pump module (30) comprising a first chamber (31) and a first piston (32) contained therein, said first piston having a first plunger (34) that, in cooperation with internal walls of said first chamber (31), defines first (35) and second (36) variable-volume sub-chambers of said first chamber (31), and a second pump module (30') comprising a second chamber (31') and a second piston (32') contained therein, said second piston having a second plunger (34') that, in cooperation with internal walls of said second chamber (31'), defines first (35') and second (36') variable-volume sub-chambers of said second chamber (31');

a first inlet fluid circuit (40) in fluid communication with said at least one first supply station (10) and with said first pump module (30) for supplying said first fluid to said first (35) and second (36) variable-volume sub-chambers of said first chamber (31);

a second inlet fluid circuit (40') in fluid communication with said at least one second supply station (10') and with said second pump module (30') for supplying said second fluid to said first (35') and second (36') variable-volume sub-chambers of said second chamber (31');

a first recirculation fluid circuit (60; 260) fluidically connecting said first (35) and second (36) variable-volume sub-chambers of said first chamber (31), and a first actuator (70; 270) for managing a fluid passage in both directions between said first (35) and second (36) variable-volume sub-chambers of said first chamber (31), said first actuator (70; 270) being part of said first recirculation fluid circuit (60).

2. The fluid delivery system (100; 100'; 100''; 200; 200'; 300; 400; 400'; 500) according to claim 1, characterized in that it further comprises a second recirculation fluid circuit (60'; 260') fluidically connecting said first (35') and second (36') variable-volume sub-chambers of said second chamber (31').

3. The fluid delivery system (100; 100'; 100''; 200; 200'; 300; 400; 400'; 500) according to claim 2, characterized in that it further comprises a second actuator (70'; 270') for managing the fluid passage in both directions between said first (35') and second (36') variable-volume sub-chambers of said second chamber (31'), said second actuator (70'; 270') being part of said second recirculation fluid circuit (60'; 260').

4. The fluid delivery system (100; 100'; 100''; 200; 200'; 300; 400; 400'; 400''; 500) according to claim 1, characterized in that the pressurizing unit (20) further comprises at least one driving unit (M; M') for reciprocating (A; A'; C; D) said first (32) and second (32') pistons within said first (31) and second (31') chambers respectively.

5. The fluid delivery system (100; 100'; 100''; 200; 200'; 300; 400; 400'; 400''; 500) according to claim 1, characterized in that it further comprises a first outlet fluid circuit (50) in fluid communication with said first pump module (30) for discharging said first fluid alternatively from said first (35) and second (36) variable-volume sub-chambers of said first chamber (31), said first outlet fluid circuit (50) being separate from said first inlet fluid circuit (40).

6. The fluid delivery system (100; 100'; 100''; 200; 200'; 300; 400; 400'; 400''; 500) according to claim 1, characterized in that it further comprises a second outlet fluid circuit (50') in fluid communication with said second pump module (30') for discharging said second fluid alternatively from said first (35') and second (36') variable-volume sub-chambers of said second chamber (31'), said second outlet fluid circuit (50') being separate from said second inlet fluid circuit (40').

7. The fluid delivery system (100; 200; 400; 400'; 400") according to claim 1, characterized in that the first pump module (30) and the second pump module (30') are arranged in parallel.

8. The fluid delivery system (100'; 100"; 200'; 300; 500) according to claim 1, characterized in that the first pump module (30) and the second pump module (30') are arranged in series.

9. The fluid delivery system (100; 100'; 100"; 300; 400; 400'; 500) according to claim 3, characterized in that said first (60) and second (60') recirculation fluid circuits and said first (70) and second (70') actuators associated thereto are external to said first (31) and second (31') chambers respectively.

10. The fluid delivery system (200; 200') according to claim 3, characterized in that said first (260) and second (260') recirculation fluid circuits and said first (270) and second (270') actuators are respectively contained within said first (31) and second (31') chambers and are integral with said first (34) and second (34') plungers of the respective first (32) and second (32') pistons.

11. The fluid delivery system (100; 100'; 100"; 200; 200'; 300; 400; 400"; 400'''; 500) according to claim 1, characterized in that said fluid delivery system is an injection system, and said first and second fluids are medical fluids selected from a liquid medicament, a drug, a diagnostically active contrast agent, a saline solution or a mixture thereof.

* * * * *